US005759774A

United States Patent [19]

Hackett et al.

[11] Patent Number: 5,759,774

[45] **Date of Patent: *Jun. 2, 1998**

[54] METHOD OF DETECTING CIRCULATING ANTIBODY TYPES USING DRIED OR LYOPHILIZED CELLS

[75] Inventors: Roger W. Hackett; Raymond P. Goodrich, Jr.; Christine M. Williams, all of Pasadena; Jon A. Olson, Pomona; Miller Cho, La Cresenta; Richard F. Galle, South Pasadena, all of Calif.

[73] Assignee: COBE Laboratories, Inc., Lakewood, Colo.

[ * ] Notice: The term of this patent shall not extend beyond the expiration date of Pat. No. 5,340,592.

[21] Appl. No.: 934,448

[22] PCT Filed: Jan. 10, 1992

[86] PCT No.: PCT/US92/00063

§ 371 Date: Sep. 11, 1992

§ 102(e) Date: Sep. 11, 1992

[87] PCT Pub. No.: WO92/11864

PCT Pub. Date: Jul. 23, 1992

Related U.S. Application Data

[63] Continuation-in-part of Ser. No. 815,893, Dec. 30, 1991, Pat. No. 5,340,592, which is a continuation of Ser. No. 195,745, May 18, 1988, abandoned.

[51] Int. Cl.[6] .............................. A01N 1/02; C12N 1/04

[52] U.S. Cl. .............................. 435/2; 424/129; 435/260

[58] Field of Search .............................. 435/2, 7.21, 7.23, 435/7.24, 29, 34, 240.2, 240.27, 172.1, 172.2, 172.3, 5, 243, 23; 424/129, 529, 450; 427/533

[56] References Cited

U.S. PATENT DOCUMENTS

| | | | |
|---|---|---|---|
| D. 298,278 | 10/1988 | Savitz et al. | 252/408 |
| D. 310,265 | 8/1990 | Mochnal et al. | 435/2 |
| 4,136,161 | 1/1979 | Falkowski et al. | 435/2 |

(List continued on next page.)

FOREIGN PATENT DOCUMENTS

| | | |
|---|---|---|
| 1144858 | 4/1983 | Canada . |
| 023431A1 | 7/1980 | European Pat. Off. . |
| 0299810A1 | 11/1980 | European Pat. Off. . |
| 066886A2 | 6/1982 | European Pat. Off. . |
| 0084102 | 7/1983 | European Pat. Off. . |
| 103139A2 | 8/1983 | European Pat. Off. . |
| 104881A2 | 9/1983 | European Pat. Off. . |
| 130708A1 | 6/1984 | European Pat. Off. . |
| 0140489 | 8/1985 | European Pat. Off. . |
| 166623A2 | 12/1986 | European Pat. Off. . |
| 228225A2 | 12/1986 | European Pat. Off. . |
| 0243818 | 4/1987 | European Pat. Off. . |
| 250137A2 | 6/1987 | European Pat. Off. . |
| 251707A1 | 6/1987 | European Pat. Off. . |
| 0266077 | 4/1988 | European Pat. Off. . |
| 297887A1 | 6/1988 | European Pat. Off. . |
| 304238A2 | 8/1988 | European Pat. Off. . |
| 367468A1 | 10/1989 | European Pat. Off. . |
| 015473A1 | 2/1990 | European Pat. Off. . |
| 0367468 | 5/1990 | European Pat. Off. . |
| 430517 | 11/1990 | European Pat. Off. . |
| 430517A | 6/1991 | European Pat. Off. . |
| 203221 | 10/1983 | German Dem. Rep. . |
| 3022278 | 6/1980 | Germany . |
| 00-A203221 | 10/1981 | Germany . |
| 3524451A1 | 7/1989 | Germany . |
| 1147166 | 7/1986 | Japan . |
| A1147166 | 7/1986 | Japan . |
| 1279356 | 7/1970 | United Kingdom . |
| 2005275 | 9/1978 | United Kingdom . |
| 2044452 | 2/1980 | United Kingdom . |
| 2101630 | 7/1982 | United Kingdom . |
| 2197468 | 9/1987 | United Kingdom . |
| 2194046 | 2/1988 | United Kingdom . |
| 2221466 | 7/1990 | United Kingdom . |
| WO8703205 | 6/1987 | WIPO . |
| WO8703374 | 6/1987 | WIPO . |
| WO8703375 | 6/1987 | WIPO . |
| WO8906542 | 7/1989 | WIPO . |
| WO9009593 | 8/1990 | WIPO . |
| WO9009594 | 8/1990 | WIPO . |
| US9200063 | 3/1992 | WIPO . |

OTHER PUBLICATIONS

A. Jonusys et al., *Mol. Immunol.*, 25(6):535–543, 1988.

B. Thomsen, et al., *J. Immunol. Meth.* 81:259–269, 1985.

J. Douillard et al. *Meth. in Enzymol.* 92:168–174, 1983.

Braylan, P. et al., "Reactif immunologique constitue par des antigenes . . . ", PR. AR, Sep. 15, 1982, N. 2,538,907 (A1).

Colaco, C.A.L.S., et al., "Mechanism xx Stabilization of Proteins xx Trehalose", Quadrant research foundation.

Crowe, J., et al., "Preservation of Dry Liposomes Does Not Require Retention of Residual Water", Proc. Nat'l Acad. Sci. vol. 84, pp. 1537–1540, Mar. 1987.

Crowe, L., et al., "Effects of Carbohydrates on Membrane Stability at Low Water Activities" Biochem. et Biophys. Acta, vol. 769 (1984), pp. 141–150.

Crowe, L., et al., "Preservation of Freeze–Dried Liposomes by Trehalose", Archives of Biochemistry and Biophysics, vol. 84, pp. 1537–1540, Mar. 1987.

Crowe, J.H., et al. "Interactions of Sugars with Membranes" Biochimica et Biophysica Acta, 947 (1988), 367–384.

(List continued on next page.)

*Primary Examiner*—John Ulm

*Attorney, Agent, or Firm*—Finnegan, Henderson, Farabow, Garrett & Dunner, L.L.P.

[57] ABSTRACT

A method is provided for qualitatively detecting in vitro the presence or absence of selected circulating antibody types using a diagnostic kit comprising reconstituted, after lyophilization or evaporative drying, red blood cell samples or other cell or cell-like material which have antigens which are recognized and bound by the selected antibody-type to be screened. Diagnostic kits containing the lyophilized blood samples according to the present invention have improved shelf life, and may comprise lyophilized samples packaged in a variety of forms convenient for manual single-test uses or automated multiple-test uses.

165 Claims, 14 Drawing Sheets

U.S. PATENT DOCUMENTS

| | | | |
|---|---|---|---|
| 4,203,724 | 5/1980 | Sawai et al. | 252/408 |
| 4,252,538 | 2/1981 | Barr | 427/336 |
| 4,275,053 | 6/1981 | Rosenfield et al. | 430/2 |
| 4,287,087 | 9/1981 | Brinkhous et al. | 252/408 |
| 4,347,311 | 8/1982 | Schmitz | 427/336 |
| 4,375,459 | 3/1983 | Manolagas | 435/2 |
| 4,426,357 | 1/1984 | Buffington et al. | 252/408 |
| 4,427,779 | 1/1984 | Reckel et al. | 425/6 |
| 4,486,315 | 12/1984 | Teipel | 427/336 |
| 4,487,839 | 12/1984 | Kamentsky | 410/2 |
| 4,499,183 | 2/1985 | Sujansky et al. | 425/6 |
| 4,596,723 | 6/1986 | Kaufman | 427/336 |
| 4,608,246 | 8/1986 | Bayer et al. | 424/11 |
| 4,659,655 | 4/1987 | Rose | 252/408 |
| 4,661,444 | 4/1987 | Li | 435/2 |
| 4,661,451 | 4/1987 | Hansen | 427/336 |
| 4,665,553 | 5/1987 | Gershman et al | 252/408 |
| 4,681,859 | 7/1987 | Kramer | 435/2 |
| 4,689,310 | 8/1987 | Kramer et al. | 435/6 |
| 4,720,787 | 1/1988 | Lipscomb | 435/6 |
| 4,731,326 | 3/1988 | Thompson et al. | 435/2 |
| 4,743,542 | 5/1988 | Graham, Jr. et al. | 427/336 |
| 4,814,275 | 3/1989 | Durda et al. | 435/2 |
| 4,816,413 | 3/1989 | Sinor et al. | 435/6 |
| 4,828,986 | 5/1989 | Smith et al. | 427/336 |
| 4,870,003 | 9/1989 | Kortright et al. | 435/5 |
| 4,874,690 | 10/1989 | Goodrich et al. | 435/2 |
| 4,906,567 | 3/1990 | Connelly | 435/2 |
| 4,959,308 | 9/1990 | Ogden | 427/336 |
| 4,963,478 | 10/1990 | Sinor et al. | 435/2 |
| 5,017,009 | 5/1991 | Schutt et al. | 435/6 |
| 5,017,342 | 5/1991 | Haberzettl et al. | 252/408 |
| 5,030,560 | 7/1991 | Sinor et al. | 435/7.21 |
| 5,059,518 | 10/1991 | Kortright et al. | 435/6 |
| 5,178,884 | 1/1993 | Goodrich et al. | 435/2 |
| 5,187,099 | 2/1993 | Healy et al. | 436/10 |
| 5,242,792 | 9/1993 | Rudolph et al. | 435/2 |

OTHER PUBLICATIONS

F Hoffman–La Roche Co., "Immunological Test Device" Dec. 9, 1974, Heading G1B, p. 302.

Giannitsis, D., et al., "Use of Stroma for the Detection of Blood–Group Antibodies by ELISA", Beitr. Infusionotherapie Klin Ernahr, vol. 18, pp. 244–245.

Leikola, J., et al., "Enzyme–Linked Antiglobulin test: An accurate and Simple Method . . . " *Transfusion*, vol. 28, No. 2, Mar.–Apr. 1980.

Ortho Pharmaceutical Corp., "Imminochemical test on curved surface", Jan. 9, 1974, Heading G1B, p. 451.

Pastoway, N., et al., "Variables affecting the enzyme–linked antiglobulin test . . . " *Medical Laboratory Sciences*, 1985, 42, 11–19.

Ramos, R.R., et al., "A latex particle assay for platelet–associated IgG" Transfusion, vol. 32, No. 3—, 1992.

Roser, B., et al., "The Glassy State Does Not Stabilize Proteins", Technical Manual, 10th Edition, 1990, p. 528.

Welcome Foundation Ltd., "Detaction of Antibodies to Viruses", Jul. 18, 1975, 1501395, Heading G1B, p. 330.

| | 1 | 2 | 3 | 4 | 5 | 6 | 7 | 8 | 9 | 10 | 11 | 12 | PROTOCOL |
|---|---|---|---|---|---|---|---|---|---|---|---|---|---|
| A | + | $+^W$ | NEG | + | + | + | $+^W$ | + | $+^W$ | + | NEG | NEG | LB:GDA (50ul) |
| B | NEG | NEG | NEG | $+^W$/NEG | + | NEG | NEG | + | + | + | NEG | + | LB:GDA (50ul) |
| C | + | $+^W$ | NEG | + | + | + | $+^W$/NEG | + | $+^W$ | + | NEG | NEG | LB:GDA (50ul) |
| D | + | $+^W$ | NEG | $+^W$/NEG | + | NEG | NEG | + | + | + | NEG | + | LB:GDA (50ul) |
| E | + | $+^W$ | NEG | + | + | + | NEG | + | $+^W$ | + | NEG | NEG | LB:GDA (50ul) |
| F | NEG | NEG | NEG | NEG | + | NEG | NEG | + | + | + | NEG | + | LB:GDA (50ul) |
| G | + | $+^W$ | NEG | + | + | + | NEG | + | $+^W$ | + | NEG | NEG | LB:GDA (50ul) |
| H | NEG | NEG | NEG | $+^W$/NEG | + | NEG | NEG | + | + | + | NEG | + | LB:GDA (50ul) |
| | STRONG + | WEAK + | NEGATIVE CONTROL | ANTI-D | ANTI-C | ANTI-c | ANTI-E | ANTI-e | ANTI-M | ANTI-N | ANTI-$P_1$ | ANTI-$Le^a$ | |
| | STRONG + | WEAK + | NEGATIVE CONTROL | ANTI-$Le^b$ | ANTI-$Fy^a$ | ANTI-$Fy^b$ | ANTI-K | ANTI-K | ANTI-S | ANTI-s | ANTI-$JK^a$ | ANTI-$JK^b$ | |

FIG. 7A

| | 1 | 2 | 3 | 4 | 5 | 6 | 7 | 8 | 9 | 10 | 11 | 12 | PROTOCOL |
|---|---|---|---|---|---|---|---|---|---|---|---|---|---|
| A | + | $+^{w}$ | NEG | + | + | + | NEG | + | $+^{w}$ | + | NEG | NEG | LB:GDA (50ul) |
| B | NOT TESTED | NOT TESTED | NOT TESTED | NEG | $+^{w}$ | NEG | NEG | + | + | + | NEG | + | LB:GDA (50ul) |
| C | + | $+^{w}$ | NEG | + | + | + | NEG | + | $+^{w}$ | + | NEG | NEG | LB:GDA (50ul) |
| D | NOT TESTED | NOT TESTED | NOT TESTED | NEG | $+^{w}$ | NEG | NEG | + | + | + | NEG | + | LB:GDA (50ul) |
| E | + | $+^{w}$ | NEG | + | $+^{w/-}$ | + | NEG | + | $+^{w}$ | + | NEG | NEG | LB:GDA (50ul) |
| F | NOT TESTED | NOT TESTED | NOT TESTED | NEG | $+^{w}$ | NEG | NEG | + | + | + | NEG | + | LB:GDA (50ul) |
| G | + | $+^{w}$ | NEG | + | + | + | NEG | + | $+^{w}$ | + | NEG | NEG | LB:GDA (50ul) |
| H | NOT TESTED | NOT TESTED | NOT TESTED | NEG | $+^{w}$ | NEG | NEG | + | + | + | NEG | + | LB:GDA (50ul) |
| | STRONG + | WEAK + | NEGATIVE CONTROL | ANTI-D | ANTI-C | ANTI-c | ANTI-E | ANTI-e | ANTI-M | ANTI-N | ANTI-$P_1$ | ANTI-$Le^a$ | |
| | STRONG + | WEAK + | NEGATIVE CONTROL | ANTI-$Le^b$ | ANTI-$Fy^a$ | ANTI-$Fy^b$ | ANTI-K | ANTI-K | ANTI-S | ANTI-s | ANTI-$JK^a$ | ANTI-$JK^b$ | |

FIG. 7B

| | 1 | 2 | 3 | 4 | 5 | 6 | 7 | 8 | 9 | 10 | 11 | 12 | PROTOCOL |
|---|---|---|---|---|---|---|---|---|---|---|---|---|---|
| A | + | $+^{w}$/NEG | NEG | + | + | + | NEG | + | $+^{w}$ | $+^{w}$/NEG | NEG | NEG | LB:GDA (50ul) |
| B | + | $+^{w}$/NEG | NEG | NEG | $+^{w}$ | NEG | NEG | + | + | + | NEG | + | LB:GDA (50ul) |
| C | + | $+^{w}$/NEG | NEG | + | + | + | NEG | + | $+^{w}$ | $+^{w}$/NEG | NEG | NEG | LB:GDA (50ul) |
| D | NOT TESTED | NOT TESTED | NOT TESTED | NEG | $+^{w}$ | NEG | NEG | + | + | + | NEG | + | LB:GDA (50ul) |
| E | + | $+^{w}$/NEG | NEG | + | + | + | NEG | + | $+^{w}$ | $+^{w}$/NEG | NEG | NEG | LB:GDA (50ul) |
| F | NOT TESTED | NOT TESTED | NOT TESTED | NEG | $+^{w}$ | NEG | NEG | + | + | $+^{w}$/NEG | NEG | + | LB:GDA (50ul) |
| G | + | $+^{w}$/NEG | NEG | + | + | + | NEG | + | $+^{w}$ | $+^{w}$/NEG | NEG | NEG | LB:GDA (50ul) |
| H | NOT TESTED | NOT TESTED | NOT TESTED | NEG | $+^{w}$ | NEG | NEG | + | + | + | NEG | + | LB:GDA (50ul) |
| | STRONG + | WEAK + | NEGATIVE CONTROL | ANTI-D | ANTI-C | ANTI-c | ANTI-E | ANTI-e | ANTI-M | ANTI-N | ANTI-$P_1$ | ANTI-$Le^a$ | |
| | STRONG + | WEAK - | NEGATIVE CONTROL | ANTI-$Le^b$ | ANTI-$Fy^a$ | ANTI-$Fy^b$ | ANTI-K | ANTI-k | ANTI-S | ANTI-s | ANTI-$JK^a$ | ANTI-$JK^b$ | |

| | 1 | 2 | 3 | 4 | 5 | 6 | 7 | 8 | 9 | 10 | 11 | 12 |
|---|---|---|---|---|---|---|---|---|---|---|---|---|
| A | + | $+^{W}$ | NEG | + | + | + | NEG | + | $+^{W}$ | $+^{W}$ | NEG | NEG |
| B | + | $+^{W}$ | NEG | NEG | $+^{W}$ | NEG | NEG | + | + | + | NEG | + |
| C | + | $+^{W}$ | NEG | + | + | + | NEG | + | $+^{W}$ | $+^{W}$ | NEG | NEG |
| D | + | $+^{W}$ | NEG | NEG | $+^{W}$ | NEG | NEG | + | + | + | NEG | + |
| E | + | $+^{W}$ | NEG | + | + | + | NEG | + | $+^{W}$ | $+^{W}$ | NEG | NEG |
| F | NEG | $+^{W}$ | NEG | NEG | $+^{W}$ | NEG | NEG | + | QNS | + | NEG | + |
| G | + | $+^{W}$ | NEG | + | + | + | NEG | + | $+^{W}$ | $+^{W}$ | NEG | NEG |
| H | + | $+^{W}$ | NEG | NEG | $+^{W}$ | NEG | NEG | $+^{W}$ | QNS | + | NEG | + |
| | STRONG + | WEAK + | NEGATIVE CONTROL | ANTI-D | ANTI-C | ANTI-c | ANTI-E | ANTI-e | ANTI-M | ANTI-N | ANTI-$P_1$ | ANTI-$Le^a$ |
| | STRONG + | WEAK + | NEGATIVE CONTROL | ANTI-$Le^b$ | ANTI-$Fy^a$ | ANTI-$Fy^b$ | ANTI-K | ANTI-k | ANTI-S | ANTI-s | ANTI-$JK^a$ | ANTI-$JK^b$ |

| | 1 | 2 | 3 | 4 | 5 | 6 | 7 | 8 | 9 | 10 | 11 | 12 |
|---|---|---|---|---|---|---|---|---|---|---|---|---|
| A | + | $+^{W}$/NEG | NEG | + | + | + | NEG | + | + | $+^{W}$ | NEG | NEG |
| B | NOT TESTED | NOT TESTED | NOT TESTED | NEG | $+^{W}$ | NEG | NEG | + | + | + | NEG | + |
| C | + | NEG | NEG | + | + | + | NEG | + | + | + | NEG | NEG |
| D | NOT TESTED | NOT TESTED | NOT TESTED | NEG | $+^{W}$ | NEG | NEG | + | + | NEG | NEG | + |
| E | + | $+^{W}$ | NEG | + | + | + | NEG | + | + | NEG | NEG | NEG |
| F | NOT TESTED | NOT TESTED | NOT TESTED | NEG | $+^{W}$ | NEG | NEG | + | $+^{W}$ | + | NEG | + |
| G | + | NEG | NEG | + | + | + | NEG | + | + | $+^{W}$ | NEG | NEG |
| H | NOT TESTED | NOT TESTED | NOT TESTED | NEG | $+^{W}$ | NEG | $+^{W}$/NEG | + | + | + | NEG | + |
| | STRONG + | WEAK + | NEGATIVE CONTROL | ANTI-D | ANTI-C | ANTI-c | ANTI-E | ANTI-e | ANTI-M | ANTI-N | ANTI-$P_1$ | ANTI-$Le^a$ |
| | NOT TESTED | NOT TESTED | NOT TESTED | ANTI-$Le^b$ | ANTI-$Fy^a$ | ANTI-$Fy^b$ | ANTI-K | ANTI-k | ANTI-S | ANTI-s | ANTI-$JK^a$ | ANTI-$JK^b$ |

FIG. 8B

| | 1 | 2 | 3 | 4 | 5 | 6 | 7 | 8 | 9 | 10 | 11 | 12 |
|---|---|---|---|---|---|---|---|---|---|---|---|---|
| A | + | $+^W$ | NEG | + | + | + | NEG | + | + | $+^W$ | NEG | NEG |
| B | NOT TESTED | NOT TESTED | NOT TESTED | NEG | $+^W$ | NEG | NEG | $+^W$ | + | + | NEG | + |
| C | + | NEG | NEG | + | + | + | NEG | + | + | $+^W$ | NEG | NEG |
| D | NOT TESTED | NOT TESTED | NOT TESTED | NEG | $+^W$ | NEG | NEG | + | + | + | NEG | + |
| E | NEG | NEG | NEG | + | + | + | NEG | + | + | NEG | NEG | NEG |
| F | NOT TESTED | NOT TESTED | NOT TESTED | NEG | NEG | NEG | NEG | + | + | + | NEG | + |
| G | NEG | NEG | NEG | + | + | + | NEG | + | + | $+^W$ | NEG | NEG |
| H | NOT TESTED | NOT TESTED | NOT TESTED | NEG | $+^W$ | NEG | NEG | + | + | + | NEG | + |
| | STRONG + | WEAK + | NEGATIVE CONTROL | ANTI-D | ANTI-C | ANTI-c | ANTI-E | ANTI-e | ANTI-M | ANTI-N | ANTI-$P_1$ | ANTI-$Le^a$ |
| | NOT TESTED | NOT TESTED | NOT TESTED | ANTI-$Le^b$ | ANTI-$Fy^a$ | ANTI-$Fy^b$ | ANTI-K | ANTI-k | ANTI-S | ANTI-s | ANTI-$JK^a$ | ANTI-$JK^b$ |

FIG. 8C

| | 1 | 2 | 3 | 4 | 5 | 6 | 7 | 8 | 9 | 10 | 11 | 12 |
|---|---|---|---|---|---|---|---|---|---|---|---|---|
| A | + | NEG | NEG | + | + | + | NEG | + | $+^W$ | $+^W$ | NEG | NEG |
| B | NOT TESTED | NOT TESTED | NOT TESTED | NEG | $+^W$ | NEG | NEG | + | + | + | NEG | + |
| C | + | NEG | NEG | + | + | + | NEG | + | $+^W$ | $+^W$ | NEG | NEG |
| D | NOT TESTED | NOT TESTED | NOT TESTED | NEG | $+^W$ | NEG | NEG | + | + | + | NEG | + |
| E | + | NEG | NEG | + | + | + | NEG | + | $+^W$ | $+^W$ | NEG | NEG |
| F | NOT TESTED | NOT TESTED | NOT TESTED | NEG | $+^W$ | NEG | NEG | + | + | + | NEG | + |
| G | + | NEG | NEG | + | + | + | NEG | + | $+^W$ | + | NEG | NEG |
| H | NOT TESTED | NOT TESTED | NOT TESTED | NEG | $+^W$ | NEG | NEG | $+^W$ | $+^W$ | + | NEG | + |
| | STRONG + | WEAK + | NEGATIVE CONTROL | ANTI-D | ANTI-C | ANTI-c | ANTI-E | ANTI-e | ANTI-M | ANTI-N | ANTI-$P_1$ | ANTI-$Le^a$ |
| | NOT TESTED | NOT TESTED | NOT TESTED | ANTI-$Le^b$ | ANTI-$Fy^a$ | ANTI-$Fy^b$ | ANTI-K | ANTI-k | ANTI-S | ANTI-s | ANTI-$JK^a$ | ANTI-$JK^b$ |

FIG. 8D

| | 1 | 2 | 3 | 4 | 5 | 6 | 7 | 8 | 9 | 10 | 11 | 12 |
|---|---|---|---|---|---|---|---|---|---|---|---|---|
| A | + | NEG | NEG | + | + | + | NEG | + | + | +w | NEG | NEG |
| B | +w/NOT TESTED | NOT TESTED | +w/NOT TESTED | NEG | +w | NEG | NEG | + | + | + | NEG | + |
| C | + | NEG | NEG | + | + | + | NEG | + | +w | +w | NEG | NEG |
| D | NOT TESTED | NOT TESTED | NOT TESTED | NEG | + | NEG | NEG | + | + | + | NEG | + |
| E | + | NEG | NEG | + | + | + | NEG | + | +w | NEG | NEG | NEG |
| F | NOT TESTED | NOT TESTED | NOT TESTED | NEG | +w | NEG | NEG | + | + | + | NEG | + |
| G | + | NEG | NEG | + | + | + | NEG | + | + | + | NEG | NEG |
| H | NOT TESTED | NOT TESTED | NOT TESTED | NEG | +w | NEG | NEG | + | + | + | NEG | + |
| | STRONG + | WEAK + | NEGATIVE CONTROL | ANTI-D | ANTI-C | ANTI-c | ANTI-E | ANTI-e | ANTI-M | ANTI-N | ANTI-$P_1$ | ANTI-$Le^a$ |
| | NOT TESTED | NOT TESTED | NOT TESTED | ANTI-$Le^b$ | ANTI-$Fy^a$ | ANTI-$Fy^b$ | ANTI-K | ANTI-k | ANTI-S | ANTI-s | ANTI-$JK^a$ | ANTI-$JK^b$ |

FIG. 8E

METHOD OF DETECTING CIRCULATING ANTIBODY TYPES USING DRIED OR LYOPHILIZED CELLS

This application is a continuation-in-part of U.S. patent application Ser. No. 815,893, filed Dec. 30, 1991 and now U.S. Pat. No. 5,340,592, which is a continuation of U.S. patent application Ser. No. 195,745, filed May 18, 1988 and abandoned.

The present invention is directed to a method for detecting in vitro the presence or absence of circulating antibody types in a plasma, serum, antiserum or hypodermal fluid using diagnostic reagents comprising dried or lyophilized cells or cell-like materials.

BACKGROUND OF THE INVENTION

For the use of blood in transfusions it is important to test for cell-antibody incompatibility to ascertain properly, for example the ABO/Rh compatibility, since improperly matched transfusions can lead to death from mismatched blood. In addition to the conventional ABO/Rh typing, there is also a series of minor red cell surface antigens (approximately 400 or more are known) which can cause immune sensitization and alloimmune reactions if the patient is repeatedly exposed to these antigens. It is therefore important to have readily available blood typing kits which can be used to test donor blood and to test the serum of potential recipients. There are generally two varieties of blood typing kits: (1) a direct typing kit containing packaged known antisera to test agglutination behavior of sample red cells from donated blood cell units; and (2) "reverse typing" kits which contain known red cell standards used to test samples of plasma from potential recipients. The present invention is particularly applicable for use in the "reverse typing" kits for diagnosing blood samples.

Available "reverse typing" kits for clinical diagnostic use for typing blood comprise vials (usually from 2 to 30 ml each) of fresh human red blood cells of a known type suspended in a preservative medium called Alsever's solution, a solution of dextrose/sodium citrate, sodium chloride and an antibiotic, such as aureomycin, in water. However, suspensions of cells in Alsever's solution are generally limited to about a seven week refrigerated shelf life. The cells cannot be stored frozen in an Alsever's suspension. This relatively short shelf life poses a problem particularly for the hospital blood bank and the users since a typical manufacturing operation of an Alsever's suspension can take as long as three to four weeks from the time of donation to the time of regulatory release of the inventory for sale. This leaves the hospital blood bank and user only an effective three to four week shelf life before the kit must be destroyed.

Furthermore hospitals must also keep samples of rare type cell standards on hand (such as AB- and rare genotype standards) which are more expensive and difficult to acquire than commonly available cell standards. These must be replaced within the three to four week effective shelf life if they are not used.

Even during the seven weeks of refrigeration of red blood cells in Alsever's suspensions, key metabolites such as ATP, are depleted and slow cell lysis occurs. There is therefore a need for providing diagnostic kits for blood typing which have longer refrigerated (or room temperature) storage lives than the refrigerated Alsever's red cell suspensions.

The present invention is useful for, but not limited to, methods for blood grouping utilizing solid surfaces. For example, a solid surface capable of supporting an immunological reaction is provided on which cells or cell-like materials containing known antigens are attached or absorbed onto the surface. This surface containing the cells or cell-like materials may then be lyophilized or dried and stored until use. After rehydration, the surface may be contacted with an unknown blood component which may contain unknown antibodies specific for the known antigen previously attached, in which case, an immune reaction will occur. A monolayer of red blood cells containing the known antigen which was first attached to the solid surface may then be optionally activated by treating with a proteolytic enzyme. Alternatively, cells can be pretreated before attachment. The protease bromelain is known to enhance certain red blood cell antigen reactions with antibodies against these antigens. This known activated cell layer may then be brought into contact with the unknown blood component, and the known antigens will undergo an immune reaction to the extent antibodies specific thereto were present in the blood component. Following a wash step to remove unbound antibodies, the cell monolayer can be exposed to sensitized red cells carrying anti-IgG on their surface, to detect any bound antibodies on the attached cell monolayer. A centrifugation step pellets unbound sensitized cells into a red pellet, which indicates a negative reaction. Bound cells form a double monolayer (positive reaction). Any resulting immunological adhered red color on the surface will indicate the presence of these specific antibodies in the blood component. Other activating enzymes include papain, trypsin, chymotrypsin, pronase, ficin and proteinase K.

Alternatively, the native cells or cell-like material containing the antigens may be attached to the solid surface, then dried or lyophilized. Upon rehydration, the surface may be contacted with a body fluid to permit an immune reaction between antibody in the unknown fluid that is specific to the antigen attached to the solid phase. A suspension comprising sensitized red blood cells may then be brought into contact with the surface, so that the latter will undergo an immune reaction to the extent that antibodies specific were present in the unknown fluid and have already been immunologically adhered to the solid surface. The resulting red color on the surface, due to adhered sensitized red cells, will indicate the presence of specific antibodies in the unknown fluid. A negative reaction is again detected by absence of adherence of the sensitized red cells.

Commercial kits are available for solid-phase antibody detection assays or tissue typing assays for blood banking use. The existing art, however, is limited in that convenient lyophilized storage in a ready-to-use format is not available, due to inability to successfully preserve and store the numerous membrane cell surface antigens in a dry state. The present invention overcomes these issues and will permit use of lyophilized cells or cell membranes in solid phase diagnostic assays of broad application and usefulness.

Among commercially available diagnostic kits, there is available a microplate assay, under the name Microtitre®, to detect anti-red cell IgG in patient sera comprising blank plates whose individual wells have been pre-coated with antibody to permit attachment of red cells. The user must rehydrate the blank plate, then add a liquid suspension of tester red cells to each well. After attaching the cell monolayer, surplus unbound cells must be removed prior to addition of patient sera. This method requires trained technician handling to properly attach the starting cell layer, and once attached the cell layer cannot be allowed to dry; the antibody detection assay must be carried through to completion.

The present invention provides lyophilized, preattached cells or cell membranes on a solid phase platform, to confer the advantages of convenient dry storage in a ready-to-use format. Using the present invention, microplates or other solid supports may be prepared having several advantages:

1) attachment of the cells, cell membranes, or cell-like material to the solid support can be carefully controlled at the manufacturing stage, rather than relying on the user, yielding more uniform product;
2) the end user of the plate need not rely on labor-intensive and costly technician time to prepare the cell monolayer prior to use;
3) the preparation of the cell monolayer requires centrifugation of microplates, and this presents engineering hurdles for automation of the assay—the present invention will eliminate this step for the end user;
4) the lyophilized plates and cells can be stored dry and are ready-to-use, an improvement over the blank plates that must be subjected to a number of procedures by the user prior to adding the test sera;
5) the attached cell monolayer comprises red cells of known type, and heretofore these are supplied in kits as refrigerated, perishable liquid reagent whereas in the present invention this vital cell layer is made as an easily stored lyophilized material.

It is an object of the present invention to provide diagnostic kits for typing blood containing freeze-dried (lyophilized) red blood cells that may be kept for 12 months or more under refrigerated conditions without substantial hemoglobin degradation (i.e., showing evidence of little oxidation of hemoglobin to methemoglobin or hemichrome, which are among the first signs of cell degeneration). Lyophilized cells may also be stored for prolonged periods at room temperature for approx. 2–3 weeks, thereby facilitating shipping.

It is a further object of the present invention to provide diagnostic blood typing kits containing evaporatively dried red blood cell samples.

It is yet another object of the present invention to provide diagnostic kits containing evaporatively dried or lyophilized red blood cells which, when reconstituted, preserve key metabolic functions such as ATP production and lactate synthesis. This reconstitution may be done without harmful effect to the red cell surface antigens.

It is an object of the present invention to provide diagnostic kits for detection of specific antibodies, by using lyophilized red blood cells coated with antihuman IgG or antihuman IgM as indicator cells in solid-phase red cell adherence assays. The antibody coated red cell reagent can be lyophilized and reconstituted without harmful effect to the marker red cells or their bound antibodies. This application pertains to any antibody-coated cell that can be lyophilized for use in diagnostic assays.

It is an object of the present invention to provide diagnostic kits for detection of antibodies against HLA (human leukocyte antigens, or major histocompatilibility antigens) antigens, for use in blood and tissue banking. The HLA antigens are expressed on the surfaces of white blood cells, such as leukocytes and lymphocytes, platelets, and to a minor extent on red blood cells. Transfusion of platelets, white blood cells, or red cells containing leukocytes can stimulate production of anti-HLA antibodies in recipients. Transplantation of tissue, bone marrow, or organs can also lead to HLA antibody production. Such alloimmunization can also occur as a result of childbirth. All of these cases of alloimmunization can potentially complicate subsequent blood transfusions. These same considerations also apply to platelet specific antigens, especially in patients who are dependent on regular platelet or blood transfusions as a consequence of side effects from chemotherapy.

It is another object of the present invention to provide instrument calibration and quality control standards for automated blood typing equipment. Automated pipetting and plate-reading machines rely on perishable and rare blood type cell standards for routine calibration and quality control. Lyophilized or dried cells prepared by this invention will extend the shelf life of these valuable control cells, and if attached to a solid support a complete panel of control cells of known types can be conveniently packaged, stored, and used during operation of the instrument with little loss of operating time. Applications include automated reverse typing of red blood cells and automated detection of unexpected antibodies in patient sera.

It is a further object of the present invention to provide diagnostic assays or calibration standards based on lyophilized cells for manual or automated biochemical reactions. The present invention permits dry storage of intact cells which after rehydration retain key cytosolic analytes and enzymatic functions. Diagnostic tests based on dried cells can obviate the need to purify individual cell components, which is a common approach in developing cell-free assays.

The present invention is applicable not only to blood typing but also to veterinary diagnostics.

SUMMARY OF THE INVENTION

The present invention is directed to methods for making diagnostic devices and methods for qualitatively detecting in vitro the presence or absence of a selected circulating antibody-type in a sample, in liquid or solid phase. In particular, for preparing solid phase devices, the present invention provides a method for making such devices, comprising the steps of attaching cells, cell membranes or cell-like material having a defined profile of cell surface antigens capable of being recognized and bound by selected antibody types, to a solid support; immersing the attached cells, cell membranes or cell-like material in a cryoprotective medium; and lyophilizing the attached cells, cell membranes and cell-like material and cryoprotective medium on the solid support, or, alternatively, evaporatively drying the cells, cell membranes or cell-like material and cryoprotective medium on the solid support.

The solid support having the attached dry cells or cell-like materials may then be stored, at ambient temperature or under refrigeration. The solid support may be wells of a microplate, dip-sticks, filters, pads, or tubes.

As described herein, the microplates are deemed to be dry if at least about 10% (wt.) of the initial water present is evaporatively removed, and preferably about 90% or more is removed.

The dried solid support may then be reconstituted and the solid support optionally washed. The reconstitution may be accomplished by reconstitution buffers or by direct rehydration using the biological fluid (plasma, serum, etc.). The reconstituted solid support is mixed with a sample of plasma, serum, anti-serum, tissue fluid, body fluid, hybridoma fluid or other sample containing the target antibodies for a sufficient period of time in a solution permissible for antibody-antigen recognition, and at a temperature to effect binding of the antigen or antigens with the antibody type or types, if present in the sample. The presence or absence of the antibody bound to the rehydrated, attached cells, membranes or cell-like materials is determined using an appropriate antibody detection method. Typically, the presence or absence of antibody binding may be detected by agglutination, secondary (indirect) antibody methods such as enzyme-linked immunosorbent (ELISA) assays, radioimmunoassays (RIA), etc. or binding of antibody coated red blood cells (red cell adherence).

The present invention further provides a diagnostic panel comprising a plurality of compartments, each containing a different lyophilized or evaporatively dried cell or cell-like material known to have one or more antigens which are recognized and bound by a selected antibody type. The cell or cell-like material is selected from the group consisting of peripheral blood cells, erythrocytes, lymphocytes, platelets, liposomes, hemosomes and cell membranes ("ghosts"). Other cell types having cell surface markers can also be used.

The present invention further provides diagnostic kits comprising such a panel of a plurality of compartments, each containing a different lyophilized or evaporatively dried cell or cell-like material as described above, and each characterized by one or more antigens which are recognized and bound by a selected antibody type.

The present invention is further directed to a method for qualitatively detecting in vitro the presence or absence of a selected circulating antibody-type in a plasma sample comprising the steps of:

(a) reconstituting at least one lyophilized standard composition, the standard composition comprising cell or cell-like material selected from the group consisting of erythrocytes, lymphocytes, platelets, liposomes and hemosomes, and isolated cell membranes containing cell surface antigens (called "ghosts") and the cell or cell-like material known to have one or more antigens which are recognized and are bound by the selected antibody-type;

(b) optionally, washing the reconstituted standard composition from step (a);

(c) mixing said reconstituted standard composition with the plasma sample for a period of time and at a temperature sufficient to allow binding of the antigen or antigens with said antibody type, if present in the sample;

(d) determining the presence or absence of antibody binding, which can be detected by determining the presence or absence of agglutination in the mixture formed from step (c).

BRIEF DESCRIPTION OF THE DRAWINGS

FIGS. 7*a*, 7*b*, 7*c* are schematic representations of screening results on microplates described in Example 7.

FIGS. 8*a*, 8*b*, 8*c*, 8*d* and 8*e* are schematic representations of screening results on microplates described in Example 8.

DESCRIPTION OF THE INVENTION

Figure 1:
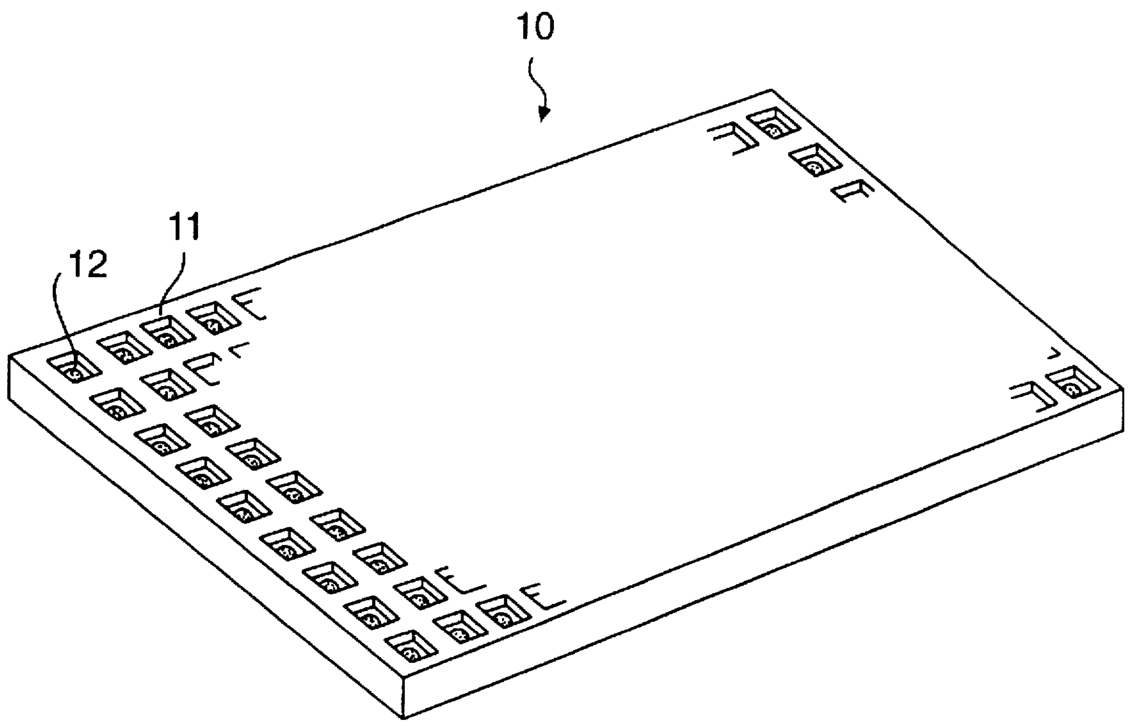
FIG. 1 is a perspective view of a microplate for use according to the present invention.

To lyophilize the cell or cell-like material which will be used as a diagnostic reagent, preferably in a diagnostic kit, briefly, a plurality of cells is immersed in an essentially aqueous protective medium, preferably containing a carbohydrate, and a mixture of at least two types of polymers, including amphipathic polymers, freezing the solution and drying the solution to yield lyophilized cells, stroma or cell-like material, which, when reconstituted, produce a significant percentage of intact and useful (i.e., antigentically and metabolically viable, in the case of cells) cells or cell-like materials. This is applicable to cells and cell-like materials which have cytosolic and/or surface membrane receptors such as cell "ghosts", liposomes and hemosomes but is preferably applied to red blood cells. This lyophilization allows for conditions which maintain the structure of the cell, biological activity of the hemoglobin, and integrity of the cell membrane and associated surface antigens.

As used herein, "cells" include, but are not limited to, red blood cells coated with antibodies, such as antihuman IgG or antihuman IgM, platelets, lymphocytes, leukocytes and cell-like materials, such as hemosomes and liposomes. The antibody coated cells can be lyophilized and reconstituted for use in diagnostic assays as indicator cells and as antibody sensitized cells such as Coombs cells. Other cells which are encompassed by the scope of the present invention include hematopoietic stem cells, cancer or hybridoma cultured cell lines, tumor cell explants, or other cultured human or mammalian cells.

As used herein, antibody-antigen binding is one kind of more general ligand receptor binding. Any ligand-receptor system found in cells may be preserved in the lyophilized cells herein and used to create storable liquid or solid phase assays. Examples include steroid hormone-receptor assays, or growth factor-receptor assays.

For intact cells the carbohydrate may be selected from the group consisting of monosaccharides, since disaccharides do not appear to permeate the membrane to any significant extent. Monosaccharide pentoses and hexoses are preferred in concentrations of from about 7.0 to 37.5%, preferably about 26% weight by volume. Xylose, glucose, ribose, mannose and fructose are employed to particular advantage.

It should be understood that monosaccharides are best suited for preserving intact lyophilized cells, but for solid phase assays in which the cells, cell membranes, or cell-like materials are attached to a solid support such that the surface antigens are not lost following cell lysis, larger impermeable carbohydrates such as disaccharides, trisaccharides, etc. may also be used. Larger membrane impermeable carbohydrates may be used to lyophilize cell membranes or cell "ghosts" (lysed cell stroma) for which cell permeability is reduced or not critical for antigen recognition.

The use of a mixture of water soluble, biologically compatible polymers, at least one type of which is amphipathic, in addition to the carbohydrate, adds significantly to the recovery of intact cells, as measured by the percentage of biologically-active hemoglobin (in the case of red blood cells) which is retained in the cells and recovered after reconstitution of red blood cells after lyophilization. The polymers will preferably be amphipathic, meaning that there are hydrophilic and hydrophobic portions on a single molecule of the polymer. The mixture of polymers may be present in the buffered lyophilization solution in total concentrations of from 0.7% (by weight) up to saturation. Preferably, each of the polymer types in the mixture has a molecular weight in the range of from about 1K to about 600K (number average molecular weight). Preferably, at least one of the types of polymers of the mixture will preferably have a molecular weight from about 5K to 400K, and most preferably from 20K to 360K. Also, one of the types of polymers of the mixture will preferably have a molecular weight in the range of about 100K to about 600K, most preferably in the range of about 100–500K. For a mixture of two different polymer types, each of the polymer types may be present in a concentration of from about 0.35% (by weight) up to its limit of solubility in the buffered lyophilization solution. Polymers selected from the group consisting of polyvinylpyrrolidone (PVP), polyvinylpyrrolidone derivatives, dextran, dextran derivatives, amino acid based polymers (i.e., proteins) and hydroxyethyl starch (HES) may be employed. Other amphipathic polymers may be used, such as poloxamers in any of their various forms. In a preferred embodiment, a mixture of PVP (molecular weight in the range of about 20K–360K) and HES (molecular weight in the range of about 100K–500K) is employed in the buffered lyophilization solution.

The use of the carbohydrate-polymer solution in the lyophilization particularly of red blood cells allows for the recovery of intact cells, a significant percentage of which contain biologically-active hemoglobin. While not intending to be bound by any theory, the amphipathic properties of the polymers allow them to bind to the cell membrane while protecting the membrane surface by extension of the hydrophilic portion into the aqueous environment. This may alleviate the damage to the cell membrane which causes other problems following reconstitution, such as cell aggregation and cell fusion, and cell lysis.

Again it is understood that use of the carbohydrate-polymer mixture to lyophilize intact cells may be also applied to cell membranes, membrane "ghosts", or cell stroma, particularly in solid phase assays in which these are attached to a solid support. While not intending to be bound by theory, lyophilization of attached cell membranes may be achieved with solutions comprising carbohydrates and one polymer species, in particular polyvinylpyrrolidone. A greater diversity of carbohydrates (i.e., mono, di, and trisaccharide) may be used to lyophilize cell membranes. Thus the preferred lyophilization buffer for intact red cells may be adapted to cell membranes.

As is shown by the embodiments set forth below, the described solutions provide media which permit cells, particularly red blood cells, to be subjected to the stresses of freezing, water sublimation and reconstitution and to form freeze-dried cells which may be reconstituted to yield cells which are capable of functioning normally, including retention of surface antigens recognizable by antibodies.

Unless indicated otherwise by the terminology or the context, all percentages set forth herein are expressed as weight percentages (i.e., weight of the solute versus the total weight of the solution).

As noted above, the process of the invention provides media for the lyophilization of erythrocytes.

The term lyophilization is broadly defined as freezing a substance and then reducing the concentration of one of the solvents, namely water, by sublimation and desorption, to levels which will no longer support biological or chemical reactions. Usually, the drying step is accomplished in a high vacuum. However, with respect to the storage of cells and particularly erythrocytes, the extent of drying (the amount of residual moisture) is of critical importance in the ability of cells, cell membranes or cell "ghosts" to withstand long-term storage at room temperature or under refrigeration. In the method described herein, cells may be lyophilized to a residual water content of less than 10%, preferably less than 5%, and most preferably to a water content of less than 3%.

Alternatively, in lieu of lyophilization, the attached cells or cell-like materials may be evaporatively dried. While the cells or cell-like materials may thus have a higher residual moisture content than that produced by lyophilization, this process requires no freeze-drying equipment, although some of the storage advantages of lyophilized products may be reduced.

The buffered lyophilization solution may contain, in addition to the monosaccharide and amphipathic polymer mixture, adjuvants, buffering agents, salts, cofactors, and the like. A particularly preferred lyophilization buffer contains the following components:

| | |
|---|---|
| 10.0 mM Glutathione (reduced) | 3.07 g/l |
| 10.0 mM Inosine | 2.68 g/l |
| 5.0 mM Adenine | 0.69 g/l |
| 0.75 mM Nicotinic acid | 0.09 g/l |
| 0.75 mM Glutamine | 0.11 g/l |
| 0.49 mM $MgCl_2 \bullet 6H_2O$ | 0.10 g/l |
| 1.47 mM $KH_2PO4$ | 0.20 g/l |
| 8.1 mM $Na_2HPO_4 \bullet 7H_2O$ | 2.17 g/l |
| 1.7 M Dextrose | 306.3 g/l |
| 3.0 wt. % PVP (m. w. 360,000); | 30 g/l |
| 15.0 wt. % M-HES (m. w. 500,000): | 150 g/l |

In a typical lyophilization procedure used to practice the present invention, whole blood or packed red blood cells to be lyophilized are washed, preferably on a cell washer (such as the COBE 2991) with dextrose saline, to yield a leukocyte-depleted packed red cell suspension.

The cells are mixed in a freezing container with lyophilization buffer at a typically useful hematocrit of 30%. For solid phase diagnostic tests, the cells are first attached to the solid support, for example, to create a monolayer of attached cells in a coupling buffer such as buffered saline, and then mixed or immersed in the appropriate dilution of lyophilization buffer. Mixing with lyophilization buffer can be achieved directly in individual microplate wells, each containing an attached cell layer.

The lyophilization buffer for intact cells is preferably as described above, with the advantages of using a polymer mixture as shown by experimentation, the results of which are set forth in Table 1. As a control, one run was performed using only 20% 24K PVP as the polymer.

The freezing container or solid support such as a microplate is then placed on the cooled shelf of a conventional shelf freeze-dryer, and the shelf temperature is lowered to freeze the cell mixture. Once frozen, a vacuum is applied and the samples are allowed to dry until the sample is thoroughly dried. To prepare diagnostic panels for use in kits, the samples may be lyophilized directly in the wells of a microplate.

To reconstitute the dried samples, an equal volume of reconstitution buffer prewarmed to 37° C. is added to samples and agitated until sample is fully hydrated. Preferably the reconstitution buffer will contain a polymer as described above in connection with the lyophilization buffer (concentration preferably in the range of about 1–20 wt. %) which is amphipathic having a MW in the range of 1–600K, preferably 1–360K. These conditions are preferred for optimum recovery of intact and metabolically viable cells having functional cell antigens, and can be used to recover intact cells in suspension for cell agglutination assays or for metabolic or biochemical assays.

A preferred reconstitution buffer to optimize recovery of intact cells is as follows:

| | |
|---|---|
| 5.0 mM ATP | 2.76 g/l |
| 1.47 mM $KH_2PO_4$ | 0.20 g/l |
| 8.1 mM $Na_2HPO_4 \cdot 7H_2O$ | 2.17 g/l |
| 19.0% 10K PVP | 190.0 g/l |

For reconstitution of intact cells into a liquid suspension (i.e., for use in conventional cell agglutination assays), reconstituted sample is prediluted with an equal volume of reconstitution buffer and agitated until thoroughly mixed. The reconstituted and prediluted cells are centrifuged at room temperature.

The cell pellet is resuspended in wash buffer and centrifuged. The wash buffer will preferably contain a polymer as described above in connection with the lyophilization buffer (concentration preferably in the range of about 1–20 wt. %) which is amphipathic having a MW in the range of 1–600K, preferably 1–360K.

The preferred wash buffer, again to optimize recovery of intact cells in liquid suspension, is as follows:

| | |
|---|---|
| 10.0 mM Inosine | 2.68 g/l |
| 5.0 mM Adenine | 0.69 g/l |
| 0.75 mM Nicotinic acid | 0.09 g/l |
| 0.75 mM Glutamine | 0.11 g/l |
| 0.49 mM $MgCl_2$ $6H_2O$ | 0.10 g/l |
| 30.0 mM KCl | 2.24 g/l |
| 30.0 mM NaCl | 1.75 g/l |
| 10.0 mM $Na_2HPO_4 \cdot 7H_2O$ | 2.68 g/l |
| 20.0 mM Glucose | 3.60 g/l |
| 16.0% 40K PVP | 160.0 g/l |

The cell pellet can optionally be resuspended in a diluent buffer at a 10–50 fold dilution and centrifuged.

The diluent buffer is as follows:

| | |
|---|---|
| 129.5 mM NaCl | 7.57 g/l |
| 5.0 mM $Na_2HPO_4 \cdot 7H_2O$ | 1.34 g/l |

The pellet is resuspended in transfusion buffer and centrifuged. This step is repeated once. The transfusion buffer will preferably contain a polymer as described above in connection with the lyophilization buffer (concentration preferably in the range of about 1–20 weight %) which is amphipathic having a Mw in the range of 1–600K, preferably 1–10K.

The preferred transfusion buffer is as follows:

| | |
|---|---|
| 77.0 mM NaCl | 4.50 g/l |
| 5.0 mM $Na_2HPO_4 \cdot 7H_2O$ | 1.34 g/l |
| 10.0 mM Glucose | 1.80 g/l |
| 10.0% 2.5K PVP | 100.0 g/l |

The preceding steps of predilution, use of wash buffer, diluent buffer, and transfusion buffer yield viable intact cells. For blood typing and antibody screening assays, however, it is only necessary that the cell surface antigens be preserved for the purpose of the assay. For solid phase assays using attached cells or cell membranes, more rapid reconstitution and washing using phosphate buffered saline can be used with effective antigen preservation.

Assays based on recovered intact red cells can take advantage of the red pigment (hemoglobin) in the cells as a convenient tracer. To determine the hemoglobin recovery in reconstituted intact red cells a 200 uL sample is centrifuged for 5 min. at 5000 rpm. The cell pellet and supernatant are separated and 180 Ul of water is added to the pellets, which are lysed by vortexing. To each sample 1 mL of Drabkins reagent is added, and after standing at R.T for 15 min. the absorbance at 540 nm is determined. Recovery=$A_{540}$ pellet/$A_{540}$ pellet+$A_{540}$ supernatant.

To determine whole blood stability of reconstituted red cells at 37° C. $^{51}Cr$ as sodium chromate in a 1 mCi/ml sterile NaCl solution is added to a sample of reconstituted cells. In this standard assay $^{51}Cr$ binds to cell hemoglobin inside the cells. 5 μCi of $^{1}Cr$ is added for every 0.1 ml of packed RBC pellet. The labelled pellet is incubated 15 min. at 37° C. after which the labelling reaction is stopped by addition of 1 ul of ascorbic acid (50 mg/ml in buffer) to every 0.1 ml of pellet. The pellet is then allowed to incubate another 5 min. at room temperature. The labelled sample is then washed 2 to 3 times in transfusion buffer. An aliquot of labelled cells is then transferred to 5 ml of autologous whole blood and the stability determined by the lysis of labelled cells at time points up to 24 hours. The amount of free $^{51}Cr$ in the supernatant after centrifuging indicates the amount of cell lysis. For convenience, a 4-hour incubation is used, since lysis (if any) is complete by then.

Cell stability data (using the $^{51}Cr$ tracer) show the stability and integrity of the lyophilized, reconstituted red blood cells. The $^{5}Cr$ binds to the internal cell hemoglobin, and is released into the assay supernatant (therefore, lost) if the cells lyse. Thus, retention of $^{51}Cr$ in the pellet measures cell integrity. The high cell stability indicates sufficient cell preservation to be useful for diagnostic use.

In another embodiment, after reconstitution, cells containing nuclei may be lysed or solubilized to release the DNA. Probes, which may be prepared by polymerase chain reaction (PCR) methodology, may then be utilized to identify presence or absence of predetermined DNA sequences. This is particularly useful to detect Major Histocompatibility Complex (MHC) alleles in chromosomes of tissues. This would infer the presence or absence of antigens encoded by the specific alleles to which the probes are designed to hybridize.

To utilize the present invention in the solid phase, it is preferred that conventional microplates be utilized where the wells are scored or otherwise treated to receive cells or cell-like materials. The cells or cell-like materials may be attached to the bottom of the wells by conventional means, such as ionic bonding, by covalent linkages (such as, glutaraldehyde linking, U.S. Pat. No. 460,246, or diazo linking, Canadian Patent No. 1,144,858, or other bifunctional chemical crosslinkers selected to vary the length of the spacer between the reactive groups), or by attaching the cells via their cell surface antigens to antibodies or lectins which have already been attached or covalently linked to the bottom of the plate. The solid support may comprise a polymeric material, such as polystyrene, which can be functionalized by known methods with coupling groups, particularly those which may be photochemically activated, or by methods using crosslinkers, such as aldehydes, maleimides, succinimides, carbodiimides or a diazonium salt, which can form a diazoamino linkage to cells, platelets, etc. Such functional groups may be attached via the benzene nucleus of plastic polymers such as polystyrene. Other coupling groups such as organic dyes may provide additional aromatic rings or electric charge to effect cell attachment. Other natural or synthetic organic or inorganic materials may be used as a solid support, such as glass, cellulose, diazobenzylcellulose, nitrocellulose, cellulose, agar, nylon, polyvinylchloride, latex, and polypropylene. Once the cells or cell-like materials are covalently linked or otherwise attached to the wells or other solid surfaces, they are contacted with one of the cryoprotectant solutions described above, then either lyophilized or evaporatively dried. The bound cells or cell-like materials may be rehydrated using one of the rehydration buffers described above or phosphate buffered saline and blood typing anti-serum or raw patient serum may be applied to each rehydrated well. After washing away unbound antibodies, a second layer of antibody sensitized indicator red cells may be applied to detect any bound antibodies. After application of the indicator cells, the plate is centrifuged to pellet unbound indicator cells. This detection method using secondary sensitized red cells to detect bound antibodies is termed red cell adherence assay.

Alternatively, after washing away unbound antibodies, any bound antibodies in each well may be detected using methods based on indirect immunoassays. In these methods secondary antibodies (such as goat anti-human IgG) or antibody fragments such as $F_c$ preparations are added that recognize any antibodies bound to the cells or cell-like materials. In a competitive immunoassay, the secondary antibody is made to compete for binding to the receptor versus the primary ligand, which itself may be an antibody.

The secondary antibodies can be conjugated with enzymes, radioactive isotopes, metal atoms, or other material capable of producing a detectable signal.

The signal so formed can comprise a solution color change, solid substrate (dipstick) color change, radioactive decay, chemiluminescent reaction, fluorescence, or other measurable change.

Alternatively, the bound antibodies may be detected using Protein A or Protein G, which bind to immunoglobulins in general. Protein A is isolated from the bacterium S. aureus. The related Protein G can be modified to remove nonspecific binding to non 25 immunoglobulin proteins. Commercial protein preparations made by recombinant DNA methods can be used. Immunoglobulin-binding proteins such as Protein A and Protein G can be conjugated to enzyme or other molecules such as biotin. Biotin is selectively bound by the protein avidin, which in turn can comprise an avidin-enzyme conjugate for the detection assay.

For ease in formulation or for efficient removal from a reaction solution by centrifugation, either the cells, cell membranes, cell-like materials, or alternatively the secondary antibody or antibody conjugate may be attached to solid particles such as pellets, beads, or microspheres.

Detection of the signal can involve manual and visual examination of each well, dipstick, pad, tube, or other reaction vessel, or alternatively involves an automated instrument designed to detect and record the presence or absence of a signal. Use of automated instruments is particularly useful for a high volume clinical laboratory as significant labor cost savings can be achieved.

A fully automated instrument for large laboratories can comprise a moving track or carousel designed to accommodate microplates, tubes, etc., combined with an automated multiple tip pipetting device for fluid dispensing or waste fluid removal. Features for reaction temperature control and mechanical agitation can also be incorporated. For the final step, an automated plate or tube reading device is used to detect the presence or absence in each microplate well or tube of the signal, particularly for detection of color change, chemiluminescence, or fluorescence. The detector often comprises a light source, optical lens, and photomultiplier light detector. The exact light source and use of filters to select specific wavelengths are tailored to the specific detection method.

Alternatively, a semi-automated system may comprise manual pipetting to conduct the assay, followed by detection and data recording by an automated table top plate reader, fluorimeter, or luminometer.

The present invention will allow the manufacture of lyophilized or dry solid phase microplate, dipstick, pad, or tube assays capable of being easily rehydrated, mixed with human serum, and monitored using an automated instrument. The present invention will also allow the manufacture of lyophilized or dry control cell standards of known antigen type, which can be used to either calibrate or quality control automated instruments or human operators.

Liquid Phase Experiments

Experiment 1

Red cell samples were lyophilized using one polymer or a polymer mixture, and the whole blood stability of $^{51}Cr$ labeled reconstituted cells was studied.

The results are described as follows in Table 1.

TABLE 1

| Lyophilization Buffer Polymer Composition | Hemoglobin Recovery | Mean Cellular Volume | 4 hr. Whole Blood Stability |
|---|---|---|---|
| 20% 24K FVP (Control) | 24.3 ± 2.2 | 87.6 ± 6.2 fl | 50.5 ± 15.5% |
| 5% 24K FVP 15% 500K HES | 27.3 ± 2.0% | 74.7 ± 11.3 fl | 73.7 ± 9.6% |
| 10% 24K PVP 10% 500K HES | 28.1 ± 2.7% | 84.3 ± 8.1 fl | 67.8 ± 95% |
| 10% 24K PVP 5% 500K HES | 23.2% | 67.0 fl | 78.7% |

It can be seen that by using a mixture of polymers the 4-hr. whole blood stability is significantly improved versus the control sample using one polymer.

Experiment 2

In an alternative test, packed red blood cells are mixed in a container with lyophilization buffer at a hematocrit of 30%. The lyophilization buffer is described below for Table 2.

The container is then placed in a standard shelf lyophilizer (Virtis SRC-15 Lyophilizer) and frozen. The frozen sample is then placed under a vacuum. The sample is lowed to dry, with a total weight loss of 58±2%. The sample is returned to room temperature and the vacuum is removed.

To reconstitute the dried samples, an equal volume of pre-warmed reconstitution buffer is added to samples and agitated until sample is fully hydrated.

The reconstitution buffer is as previously described.

The reconstituted sample is prediluted with an equal volume of reconstitution buffer and swirled until thoroughly mixed. The reconstituted and prediluted cells are transferred to a COBE 2991 Blood Cell Washer, centrifuged, and repeated until all of the reconstitution buffer volume is added to the Cobe bag. The cells are washed by the automatic protocol of the Cell Washer with the following solutions described in Example 1:

1. Wash buffer: 500 ml.
2. Pellets washed with Diluent buffer: 500 ml.
3. Transfusion buffer: 500 ml.

All samples are 30% hematocrit in Table 2. The lyophilization buffer used to prepare the samples in Table 2 contained a mixture of 3% 360K PVP and 15% 500K HES.

TABLE 2

| Sample No. | % Hb Recovery | MCV | % Whole Blood Stability |
|---|---|---|---|
| 1 | 27.3 | 80.0 | 73.3 |
| 2 | 26.2 | 76.1 | 73.3 |
| 3 | 29.6 | 78.7 | 62.5 |
| 4 | 27.2 | 80.5 | 70.9 |
| 5 | 29.4 | 76.1 | 70.6 |
| 6 | 24.7 | 76.1 | 71.7 |
| 7 | 26.5 | 80.0 | 68.2 |
| MEAN | 27.3 ± 1.77 | 78.2 ± 2.0 $\mu m^3$ | 70.1 ± 3.8 |

Note: MCV = mean cell volume

Experiment 3

A test was repeated with the substitution of 200K HES for 500K HES in a given HES/PVP polymer mixture in the lyophilization buffer. The results are described in Table 3.

TABLE 3

| Lyophilization Buffer Polymer Composition | Hemoglobin Recovery | Mean Cellular Volume | 4 hr. Whole Blood Stability |
|---|---|---|---|
| 5% 24K PVP 10% 200K HES | 14.7% | 77.3 fl | 65.1% |
| 10% 24K PVP 10% 200K HES | 27.7 ± 4.4% | 81.8 ± 1.8 fl | 61.6% |

The whole blood stability is reduced if the cells are lyophilized using the 200K HES, compared to using 500K HES as in Table 2.

Experiment 4

In a test for 40% hematocrit mixtures with washed red blood cells, the polymer composition used in these lyophilization buffers, was 5:15% 24K PVP:500K HES. The glucose concentration in the 40% lyophilization buffers is increased to 2.3 M (441.37 g/l). All other conditions were the same as those in Example 1. The results are described as follows in Table 4:

TABLE 4

| Sample Hct. | Lyophilization Buffer Polymer Composition | Hemoglobin Recovery | Mean Cellular Volume | 4 hr. Whole Blood Stability |
|---|---|---|---|---|
| 40% | 20% 24K PVP (Control) | 28.2 ± 3.5% | 80.0 ± 7.9 fl | 39.5 ± 1.0% |
| 40% | 5% 24K PVP 15% 500K HES | 29.2 ± 3.0% | 82.9 ± 12.9 fl | 70.1 ± 14.8% |

The 4-hr. whole blood stability was significantly increased using a polymer mixture as compared to using a single polymer.

Experiment 5

Using 360K PVP instead of 24K PVP in a given HES/PVP polymer mixture in the lyophilization buffer, the test was repeated. The results are described in Table 5.

TABLE 5

| Lyophilization Buffer Polymer Composition | Hemoglobin Recovery | Mean Cellular Volume | 4 hr. Whole Blood Stability |
|---|---|---|---|
| 3% 360K PVP 15% 500K HES | 24 ± 6% | 79 ± 6 fl | 76 ± 10% |

Solid Phase Experiments.

Referring to the FIG. 1 there is shown a microplate 10 having a plurality of wells 11. A conventional microplate will have 96 wells. At the bottom of each well is a cake 12 of lyophilized red blood cells. The cake may comprise free cells to be later dehydrated for agglutination assays, or cells attached to the solid support for use in solid phase immunoassays. Plate 10 may contain only one cell type (such as O+, AB−, etc.), or may have coded sectors, including color-coded sectors, containing a different cell type in each sector, such as having an eight sector plate comprising cells having each of the major types of blood combination A−, A+, B−, B+, O−, O+, AB−, AB+. Each well 11 may be made capable of being scored for agglutination. Scorable surfaces for this purpose are known in the art, such as, etched chips of glass. Alternatively, the plate 10 may contain cells with rare profiles of selected minor antigens such as s/k/m/c+, etc. In another design, each well in plate 10 may contain a pool of cells having a different spectrum of surface antigens, such that the noted cells comprise all standard clinically significant antigens. Such a cell pool can be used to screen for unexpected patient antibodies prior to blood transfusion. No single donor's cells carries all of the common rare blood type antigens. Again, different pools of various selected cell types may be arranged on the plate according to color-coded sections.

To prepare the plate 10 preferably, a sample of the blood cells, preferably premixed into the lyophilization buffer, will be placed into each well and the plate containing the samples will be placed in a lyophilizer. After lyophilization, the plate may be sealed using a convenient means such as a foil layer under vacuum or an inert gas or by using a commercially available plate cover (not shown). The sealed plate will preferably be kept refrigerated and may be kept in that stage for a year or even more. The sealed plate can be stored at room temperatures for up to 2 to 3 weeks, thereby facilitating shipping. To use the plate the cover or seal is removed and the lyophilized red blood cells are reconstituted using the buffers as described above or reconstituted using a saline solution, particularly if the cells or cell membranes are attached to the plate. Then the plasma or serum samples containing the unknown antibodies are added to the desired wells in which the test is to be conducted. This addition may be made by for example a conventional microtip dispenser, usually containing 96 microtips or 8 tips for a 8×12 well plate. Subsequent to reconstitution, one or more wash steps may be utilized by repeated pipetting and decanting of solution or alternatively by using a micro centrifuge to spin the plates. However if some cell lysis can be tolerated in the antibody reaction, no cell washes may be needed. Furthermore, the dried cells may be rehydrated directly with antisera or patient sera, or with sera prediluted with saline solution.

In another embodiment, the red blood cells may be lyophilized to form dry beads, pellets or droplets, and packaged in compartmented blister packs or glass vials.

To the rehydrated, optionally washed cells are added samples of serum or plasma from the blood units to be typed. The microplate configuration can have convenient numerical labels or bar codes (not shown) to aid identification. In the case of cell agglutination assays, strong antibody-antigen reactions become readily reliable when positive cells are exposed to sufficient antibody and the cell clumps are allowed to settle by gravity or by centrifugation of the plate. Following incubation, usually for several minutes at room temperature, the plates can then be read, for example by automatic equipment which is readily available to read agglutination or by visual microscopic inspection for agglutination. Incubation periods and temperatures sufficient to allow agglutination are readily determined by those of ordinary skill in the art. An automated instrument may be programmed for incubation time and temperature.

In another embodiment red blood cells, such as rare cell types with unique antigen profiles may be packed in blister packs for single use to avoid wasting an entire microplate for testing a few rare units.

In another embodiment, red blood cells coated with antibodies can be lyophilized and reconstituted for use as markers in solid-phase microplate assays to detect anti-red cell antibodies, type platelets and detect antiplatelet antibodies or anti-HLA antibodies prior to platelet transfusion. The lyophilized antibody-coated red blood cells can be packed in microplates or blister packs for this application. (i.e., lyophilized Coombs test cells or lyophilized antibody-sensitized red cells for use as indicator cells in solid phase red cell adherence assays).

The solid supported lyophilized cells (or other platelets, hemosomes, and the like) may also be in the form of a membrane or membrane strip carrying the cells, cell membranes, or cell-like materials and detection of array results may be accomplished visually or optically (absorption, scatter, reflection, optical density, fluorescence, chemiluminescence, etc.)

In a particularly preferred embodiment, a diagnostic panel may be prepared using a plurality of compartments or sectors, each containing a different lyophilized cell, cell membrane or cell-like material as a standard composition attached to a solid support. The cells may be attached to the solid support through antibodies, such as antibodies which recognize and bind to specific cell surface antigens such as anti-red cell antibodies, antiplatelet antibodies or antileukocyte antibodies. Antibodies that have a general ability to bind mammalian or other cell types may also be used. The panel may be, for example, a plastic microplate comprising polystyrene or other solid materials as described hereinabove. The plastic material in a microplate, dipstick, or other solid support may be further modified to permit covalent attachment of cells, cell-like materials, cell membranes, or purified cell components such as proteins. Polystyrene in particular has a repeating benzene group in the polymer, and this group can be modified to carry diazonium groups capable of forming covalent linkages. Use of bifunctional crosslinking agents such as aldehydes or maleimides can also be incorporated. The length of the spacer segment that separates the reactive crosslinker groups can be varied (i.e., C4, C5, C6, C7 . . . etc.) to facilitate effective attachment by reducing steric hindrance.

Part of the linking or cell attachment agent may also contain an organic dye which will serve to absorb the cells, cell membranes, or cell-like materials via hydrophobic or electric charge interactions with cell surface components.

To use such a panel, it may be useful to subject the reconstituted cells to treatments to enhance the binding of the antibody types. The cells may also be protected before attachment to a surface and lyophilization, so that the are pre-sensitized upon rehydration. Such treatments may include exposure to proteolytic enzymes, detergents, chemical fixatives, low ionic strength saline, high ionic strength saline, high molecular weight polymers, and the like. The detection may also utilize the use of secondary antibodies or antibody-conjugates which amplify the sensitivity of the assay detection. Such secondary antibodies may comprise antibodies directed against IgG or IgM, or for example, polyvalent antibodies to detect heavy chain classes. The antibody conjugates may comprise antibody-radioisotope conjugates containing such commonly used radioisotopes as $^{125}I$, $^{131}I$, $^{3}H$, $^{14}C$, $^{35}S$. Other antibody conjugates include antibody-enzyme conjugates that may comprise alkaline phosphatase, horseradish peroxidase, beta-D-glactocsidase or glucose oxidase. Often the conjugates comprise antibodies conjugated with fluorochrome dyes such as rhodamine, fluorescein or phycobiliproteins. The detection systems may be the common ELISA (enzyme-linked immunosorbent assay), or may use antibody-enzyme conjugates comprising enzyme-metals such as colloidal gold or iron conjugates. A particularly preferred detection system utilizes antibody-sensitized red blood cells. Other types of reactions may be utilized such as cytotoxicity reactions, chemiluminescence reactions and the other optical methods described hereinabove.

In a particularly preferred embodiment of the invention, the detection system will comprise automated machinery which, for example, utilizes automated mechanical pipetting to manipulate the fluid samples, liquid reaction reagents for the washing or detection system and/or secondary antibody solutions previously described. When the ligand receptor complex comprises an optically detectable complex such as a fluorochrome dye, it is preferred that the automated system include, in addition to the mechanical pipetting system, the optical system comprising the incident light utilized to excite the dye, and the optical prism and photomultiplier devices used to detect the excited dyes. When an antibody enzyme conjugate capable of forming a colored reaction product is used, the optical system may comprise a light source and intervening filters to enchance detection of the colored reaction product by the light detector. Alternatively, the automated system may include the automated use of panels of bound antibodies to detect cell agglutination indicating positive or negative results on the ligand-receptor binding reaction. In this case an incident light beam is blocked by unbound cells or cell agglutination clumps, depending on how detection is designed into the assay.

In another embodiment, the lyophilization medium or any of the reconstitution or wash solutions may be adjusted so that the reconstituted cells or cell-like materials are incubated with antibodies (either antisera or plasma or serum from blood) in an incubation medium that optimizes a desired antibody-antigen reaction. For example, certain reactions are enhanced at lower pH or ionic strength, or by a polymer such as PEG (polyethlyeneglycol). The enhancer may be a polymer, such as PEG, a protein, such as BSA, or other macromolecular species.

The present invention is applicable to antibody-coated cells, including mammalian and human cells. Preferably the antibody-coated cells may be coated with fluorescently tagged antibodies where the antibodies are derived from polyclonal sera or monoclonal antibodies derived from hybridoma cultures. These fluorescently tagged antibodies which comprise the coatings on the cells may be utilized as calibration standards for cell sorting, cell counting, or analytical cytometry, such as flow cytometry or other types of analytical cytometry methods.

In another embodiment, the antibody-coated cells may comprise red blood cells coated with antibodies against human IgG or IgM (sensitized or indicator red cells, also known as Coombs check cells). These cells can be used to detect the presence of bound IgG or IgM, as the anti-IgG or anti-IgM coating enables the cells to stick to bound IgG or IgM, which can be monitored via the cells' natural red color.

As described above, in addition to red blood cells, the present invention may be used, for example, for tissue typing using other types of cells such as lymphocytes which carry HLA (Human Leukocyte Antigens) antigens. This may be used exactly as described above for red blood cells for typing prior to tissue transplantation or platelet transfusion. Artificial cell systems that include a lipid membrane such as liposomes and hemosomes which comprise antigen-carrying lipid vesicles may be utilized. Furthermore, the present invention may be utilized on cellular membranes, particularly purified cellular membranes. The membranes may be any type of cell membranes but in particular mammalian or human cell membranes. Such membranes may be prepared by conventional methods from erythrocytes, lymphocytes, platelets, peripheral blood cells, stem cells and the like. A simple method involves hypotonic lysis of intact cells, which yields residual empty cell "ghosts" comprised of all membrane, cytoskeleton, end integral and peripheral membrane associated proteins.

The intact lyophilized cells, after reconstitution, may also be useful for assays of cell metabolites, enzyme activity, ligand binding, or assays of other cell cytosol components, in assay formats as described, for example in European Patent Application 84-303827.4, incorporated by reference herein. The ligands detected include, for example, steroid hormones, growth factors, proteins, peptides, and inorganic or organic compounds such as trace elements, cofactors, nucleotides, toxins, drugs, nucleic acids, and metabolic products of drugs or toxins.

Lyophilized cells, cell membranes, or cell-like materials attached to a solid support can also be rehydrated and used as control cell panels for quality control of automated antibody detection assays. For example, panels of known cell antigen type can be constructed to cover the major blood groups (ABO) and Rh types (C, D, E, c, e) for use with reagent antisera to provide positive and negative assay controls.

The following examples are provided by way of illustration and are not intended to limit the invention in any way.

EXAMPLES

Example 1

Agglutination Assay with Human Red Cells

A unit of packed human RBC's was washed on the Cobe Cell Washer according to the standard washing procedure in the Cobe Operator's Handbook for a 2L wash in Dextrose Saline (0.2% dextrose, 0.9% NaCl). The packed RB's were then mixed with Lyophilization Buffer (0.75 mM nicotinic acid, 10 mM inosine, 5 mM adenine, 2 mM KCl, 1.47 mM $KH_2PO_4$, 75 mM NaCl, 8.1 mM $Na_2HPO_4$, 0.75 mM glutamine, 0.49 mM $MgCl_2$, 2.3M dextrose, 3% PVP m.w. 360,000, 15% M-HES m.w. 500,000) at a 40% hematocrit. The mixture was then mixed on a wrist-action shaker and then transferred to a lyophilization flask. The flask was frozen to −70° C. and vacuum dried on a Labconco Freeze Dryer.

After the sample was lyophilized, a volume of +37° C. Reconstitution Buffer (1.47 mM KH2PO4, 8.1 mM $Na_2HPO_4$, 5 mM ATP, 19% PVP m.w. 10,000) equal to 1.7 times the initial volume was added. The reconstituted RBC's were spun at 3400 rpm for 15 minutes and the supernatant was removed. The RBC's were then diluted in Wash Buffer (5 mM adenine, 10 mM inosine, 0.75 mM nicotinic acid, 0.49 mM $MgCl_2$, 20 mM glucose, 0.75 mM glutamine, 16% PVP m.w. 40,000, 10.3 mM $Na_2HPO_4$, 30 mM NaCl, 30 mM Kcl) and centrifuged at 3400 rpm for 12 minutes. The sample was then suspended in Transfusion Buffer (10 mM glucose, 77 mM NaCl, 5 mM $Na_2HPO_4$, 10% PVP m.w. 2500) and centrifuged at 1800 rpm for 10 minutes and repeated. The RBC's were then washed in Isolation Buffer (5 mM $Na_2HPO_4$, 213 mM NaCl) and spun at 1800 rpm for 10 minutes. The pellet was then resuspended in Transfusion Buffer and centrifuged at 1800 rpm for 10 minutes. All washes were at a 10 fold dilution.

The reconstituted RBC's were then analyzed for cell surface antigens following the procedural outlines included in the typing reagents purchased from Dade 10 Division of Baxter Healthcare Corp. Blood grouping reagents Anti-S, Anti-K, Anti-k', and Anti-Fya were used in an indirect antiglobulin test, whereby the reagents were mixed with a test cell suspension, incubated for 30–60 minutes at +37° C. in a dry incubator, washed to remove any unbound antibody, and an anti-human globulin added to the cells before examining macroscopically for agglutination. Blood grouping reagents Anti-c', Anti-C, Anti-E, Anti-CDE, Anti-M and Anti-P1 were used as a direct antiglobulin tube test. The reagents were mixed with a test cell suspension and examined for macroscopic agglutination following the respective incubation period or no incubation required for Anti-c', Anti-C, Anti-E and Anti-CDE. Reactions were evaluated using washed non-lyophilized cells in dextrose saline and Transfusion Buffer and lyophilized cells in Transfusion Buffer.

Reactions of the blood grouping reagents and test cells were scored on the basis of positive agglutination if the respective surface antigen was present or negative (i.e., no agglutination, confirmed by microscopic examination) if the respective surface antigen was not detectable or absent.

Negative reactions were then confirmed by continuing with an indirect antiglobin test (IAT) as described above. Samples that remained negative at the IAT stage were unambiguously confirmed by adding control antibody-coated red cells (Coombs check cells), to show that the agglutination assay was competent to detect control sensitized cells. These standard test procedures are described in the Technical Manual published by the American Association of Blood Banks.

Control samples (labelled "fresh") of fresh, nonlyophilized red blood cells from the identical units were tested in parallel with the lyophilized reconstituted samples for antibody agglutination.

Lyophilized units of packed human red blood cells (n=170) have been tested against the same fresh cells for ABO and Rh (or D antigen) grouping for all blood type combinations (A−, A+, B−, B+, O−, O+, AB−, AB+). No differences in the ABO or Rh groupings were found between fresh and lyophilized cells. Due to these results, other cell surface antigens were tested, which are shown in the following Table 6.

TABLE 6

RESULTS FROM ANTIGEN TESTING

| Unit # | S | K | k' | $Fy^a$ | $P_1$ | M | c' | C | E | CDE |
|---|---|---|---|---|---|---|---|---|---|---|
| 90-1190 Fresh | + | neg | + | + | + | + | + | neg | neg | neg |
| 90-1190 Lyoph | + | neg | + | + | + | + | + | neg | neg | neg |
| 90-1192 Fresh | + | neg | + | neg | neg | + | + | + | neg | + |
| 90-1192 Lyoph | + | neg | + | neg | neg | + | + | + | neg | + |
| 90-1193 Fresh | + | + | + | + | + | + | + | + | neg | + |
| 90-1193 Lyoph | + | + | + | + | + | + | + | + | neg | + |
| 90-1195 Fresh | + | neg | + | + | neg | + | + | neg | + | + |
| 90-1195 Lyoph | + | neg | + | + | neg | + | + | neg | + | + |
| 90-1202 Fresh | + | neg | + | + | + | + | + | + | + | + |
| 90-1202 Lyoph | + | neg | + | + | + | + | + | + | + | + |
| 90-1202 Fresh | + | neg | + | + | + | + | + | neg | neg | neg |
| 90-1203 Lyoph | + | neg | + | + | + | + | + | neg | neg | neg |

The non-lyophilized and lyophilized cells were suspended in Transfusion Buffer for analysis.
Antigen Abbreviations:
c'-hr'
C-rh'
E-rh'
D-$Rh_o$
$Fy^a$-Duffy (sub) a
K-Kell
k'-Cellano

Example 2

Cynomolgus Macaque whole blood was drawn in CPDA and washed three times in phosphate buffered saline (2.0 mM Kcl, 1.5 mM $KH_2PO_4$, 142 mM NaCl, 8.0 mM $Na_2HPO_4$) with the plasma and buf fy coat removed. The packed RBC's were then mixed at room temperature with Lyophilization Buffer (16% PVP m.w. 40,000, 2.3M glucose, 12.5 mM pyruvate, 10 mM inosine, 5 mM adenine, 5 mM Kcl, 75 mM NaCl, 10 mM Na2HPO4) at a 10% hematocrit. The mixture was then frozen to −70° C. and then placed in liquid nitrogen. The frozen sample was then vacuum dried on a Labconco Freeze Dryer. After the sample was lyophilized, an equal volume of +37° C. Reconstitution Buffer (2.0 mM Kcl, 1.5 mM $KH_2PO_4$, 110 mM NaCl, 7.8 mM $Na_2HPO_4$, 19% PVP m.w. 10,000) as the initial volume was added. After the sample was reconstituted, a second volume of Wash Buffer (12.5 mM pyruvate, 10 mM inosine, 5 mM adenine, 5 mM KCl, 75 mM NaCl, 10 mM $Na_2HPO_4$, 0.7 mM NAD, 0.49 mM $MgCl_2$, 20 mM glucose) was added. The sample was then spun at 1800 rcf for 15 minutes and the supernatant was removed. The sample was washed twice in Wash Buffer at 1800 rcf for 12 minutes. The pellet was then suspended in Diluent Buffer (1.19 mM Kcl, 4.86 mM Na2HPO4, 0.88 mM KH2PO4, 61.05 mM Na4P2O7, 8.89 mM ATP, 1% PEG m.w. 3500), and the sample was spun at 350 rcf for 10 minutes. The pellet was then incubated at +37° C. for 20 minutes. The RBC's were then washed three times in Transfusion Buffer (2 mM Kcl, 1.5 mM $KH_2PO_4$, 112 mM NaCl, 8.0 mM $Na_2HPO_4$, 10% PVP m.w. 2500) and spun at 350 rcf for 10 minutes. All washes were at a 10 fold dilution. The hemoglobin recovery was determined at each wash. A number of assays were performed on the lyophilized, reconstituted RBC's, shown in Table 7:

TABLE 7

Macaque Red Blood Cells

| | Normal | Lyophilized n = 5 |
|---|---|---|
| Metabolism: | | |
| ATP (umol/g Hb) | 3.9 ± 15 | 2.68 ± 1.7 |
| Lactate (umol/g Hb) | | |
| 0 hr | 4.5 | 8.2 |
| 2 hr | 37.8 | 7.2 |
| Indices: | | |
| MCV (cu microns) | 65.1 ± 1.06 | 68.0 ± 5.3 |
| MCH (pg) | 19.4 ± 1.0 | 11.6 ± 1.4 |
| MCHC (%) | 29.9 ± 1.3 | 17.0 ± 1.5 |
| Hemoglobin Recovery (%) | — | 22.7 ± 6.3 |
| Hemoglobin Quality: | | |
| Oxyhemoglobin (%) | 99.0 | 91.8 ± 0.9 |
| Methemoglobin (%) | 1.0 | 6.35 ± 1.1 |
| Hemichrome (%) | 0.0 | 1.8 ± 12.0 |
| $P_{50}$ (mm Hg) | 34.2 ± 1.6 | 31.9 ± 2.2 |

Example 3

Porcine whole blood was collected in CPDA and washed three times in phosphate buffered saline (2 mM KCl, 1.5 mM $KH_2PO_4$, 142 mM NaCl, 8 mM $Na_2HPO_4$) with the plasma and buffy coat removed. The packed RBC's were then mixed at room temperature with Lyophilization Buffer (16% PVP m.w. 40000, 2.3M glucose, 12.5 mM pyruvate, 10 mM inosine, 5 mM adenine, 5 mM KCl, 75 mM NaCl, 10 mM $Na_2HPO_4$) at a 10% hematocrit. The sample was then frozen to −70° C. and then placed in liquid nitrogen. The frozen sample was then placed on a Labconco Freeze Dryer and dried. The lyophilized RBC's were then reconstituted with +37° C. Reconstitution Buffer (2 mM KCl, 1.5 mM $KH_2PO_4$, 110 mM NaCl, 7.8 mM $Na_2HPO_4$, 19% PVP m.w. 10,000) in an equal volume as the initial lyophilization/RBC mixture. Another volume of Reconstitution Buffer was then added and the RBC's were then centrifuged at 1800 rcf for 15 minutes. The supernatant was then removed. Two washes were then completed using Wash Buffer (12.5 mM pyruvate, 10 mM inosine, 5 mM adenine, 5 mM KCl, 75 mM NaCl, 10 mM $Na_2HPO_4$, 0.7 mM NAD, 0.5 mM $MgCl_2$, 20 mM glucose). The mixture was centrifuged at 1800 rcf for 15 minutes. The pellet was then suspended in Diluent Buffer (1.19 mM KCl, 4.86 mM $Na_2HPO_4$, 0.88 mM $KH_2PO_4$, 61.05 mM $N_4P_2O_7$, 8.89 mM ATP, 1% PEG m.w.3500) and centrifuged at 350 rcf for 10 minutes. The pellet was incubated at +37° C. for 20 minutes. The packed RBC's were then washed three times in Transfusion Buffer (2 mM KCl, 1.5 mM $KH_2PO_4$, 112 mM NaCl, 8 mM $Na_2HPO_4$, 10% PVP m.w. 2500) and spun at 350 rcf for 10 minutes. All the washes were performed at a 10 fold dilution. The hemoglobin recovery was performed at each step in the washing procedure. The following assays were then performed, shown in Table 8:

TABLE 8

Procine Red Blood Cells

| | Normal | Lyophilized n = 17 |
|---|---|---|
| Metabolism: | | |
| ATP (umol/g Hb) | 5.08 | 5.05 ± 1.2 |
| Lactate (umol/g Hb) | | |
| 0 hr | 19.72 | 10.4 ± 4.3 |
| 2 hr | 13.17 | 7.3 ± 3.4 |
| 2.3 DPG (umol/g Hb) | 13.77 | 6.62 |
| Indices: | | |
| MCV (cu microns) | 50–68 | 45.4 ± 3.8 |
| MCH (pg) | 17–21 | 9.0 ± 0.9 |
| MCHC (%) | 30–34 | 19.9 ± 1.8 |
| Hemoglobin Recovery (%) | — | 24.1 ± 4.5 |
| Hemoglobin Quality: | | |
| Oxyhemoglobin (%) | 100.0 | 93.2 ± 2.3 |
| Methemoglobin (%) | 0.0 | 6.7 ± 2.4 |
| Hemichrome (%) | 0.0 | 0.0 |
| $P_{50}$ (mm Hg) | 33.4 ± 30.6 | 20.8 ± 2.7 |

Example 4

Chimpanzee whole blood was collected in CPDA and washed 3 times in dextrose saline (0.9% NaCl, 0.2% dextrose) with the plasma and buffy coat removed.

The packed RBC's were then mixed at room temperature with Lyophilization Buffer (2 mM KCl, 1.47 mM $KH_2PO_4$, 91.9 mM NaCl, 8.1 mM $Na_2HPO_4$, 10 mM inosine, 5 mM adenine, 0.75 mM nicotinic acid, 0.75 mM glutamine, 0.49 mM $MgCl_2$, 2.3M glucose, 5% PVP m.w. 24,000, 15% M-HES m.w. 500,000) at a 30 or 40% hematocrit. The RBC's were then frozen to −70° C. and then dried on the Labconco Freeze Dryer or on a Virtis shelf lyophilizer. The dried RBC's were then reconstituted with an equal volume as the initial RBC/lyophilization buffer mixture of +37° C. Reconstitution Buffer (2 mM KCl, 1.47 mM $KH_2PO_4$, 110.7 mM NaCl, 8.1 mM $Na_2HPO_4$, 19% PVP m.w. 10,000). Another volume of Reconstitution Buffer was then added and the RBC's were then centrifuged at 3400 rpm for 15 minutes. The sample with then suspended in Wash Buffer (0.75 mM nicotinic acid, 10 mM inosine, 5 mM adenine, 5 mM KCl, 75 mM NaCl, 10 mM $Na_2HPO_4$, 0.75 mM glutamine, 0.49 mM $MgCl_2$, 20 mM glucose, 10% PVP m.w. 24,000) and then centrifuged at 3300 rpm for 12 minutes. The pellet was then suspended in a Diluent Buffer (1.19 mM KCl, 4.86 mM Na2HPO4, 0.88 mM KH2PO4, 61 mM Na4P2O7, 8.89 mM ATP, 11 mM NaCl), and spun at 1500 rpm for 10 minutes. The final three washes were completed in Transfusion Buffer (10 mM glucose, 5 mM $Na_2HPO_4$, 10% PVP m.w. 2500, 68.4 mM NaCl) and centrifuged at 1500 rpm for 10 minutes. All washes were at a 10 fold dilution. The hemoglobin recovery was performed at each step in the processing. The following analyses were completed on the lyophilized, reconstituted samples, shown in Table 9:

TABLE 9

Chimpanzee Red Blood Cells

| | Normal | Lyophilized n = 11 |
|---|---|---|
| Metabolism: | | |
| ATP (umol/g Hb) | 3.20 ± 0.63 | 4.59 ± 1.26 |
| Lactate (umol/g Hb) | | |
| 0 hr | 14.14 ± 8.36 | 13.73 ± 8.3 |
| 2 hr | — | 13.76 ± 6.6 |
| Indices: | | |
| MCV (cu microns) | 80.6 ± 2.52 | 87.7 ± 6.9 |
| MCH (pg) | 26.1 ± 0.56 | 16.4 ± 1.4 |
| MCHC (%) | 32.4 ± 0.76 | 18.8 ± 1.6 |
| Hemoglobin Recovery (%) | — | 32.2 ± 5.7 |
| Hemoglobin Quality: | | |
| Oxyhemoglobin (%) | 99.58 ± 0.71 | 98.7 ± 0.99 |
| Methemoglobin (%) | 0.33 ± 0.72 | 0.93 ± 1.15 |
| Hemichrome (%) | 0.10 ± 0.23 | 0.30 ± 0.45 |
| Cell Density | 1.095 ± 0.003 | 1.083 ± 0.002 |
| Osmotic Stability | 97.85 ± 1.23 | 15.0 ± 6.9 |

Example 5

Shelf Life Studies at Room Temperature and Refrigerated

Figure 2:
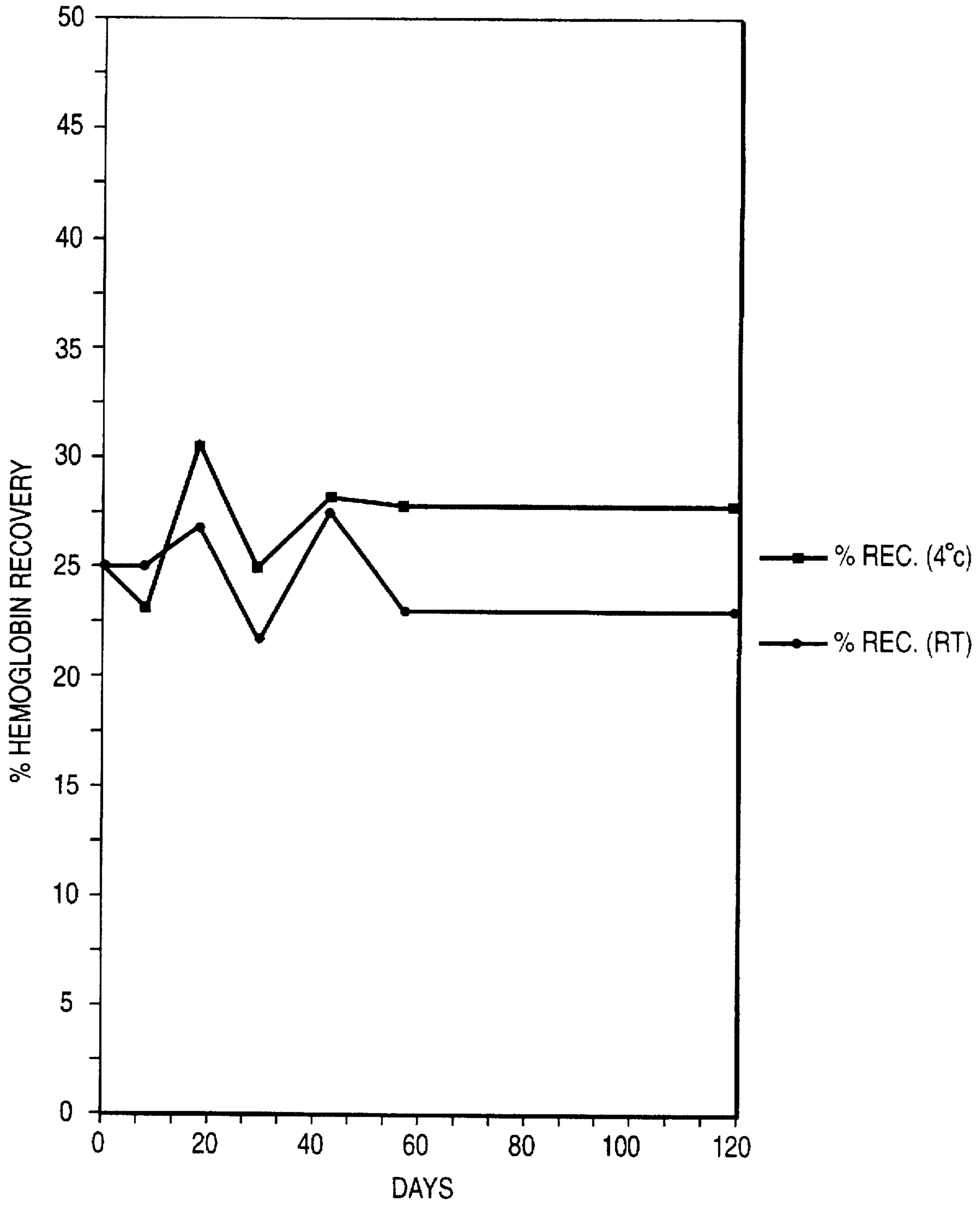
FIG. 2 is a plot of total hemoglobin recovery over time for two lyophilized erythrocyte samples stored at room temperature and 4° C., respectively, and then reconstituted and assayed.
Figure 3:
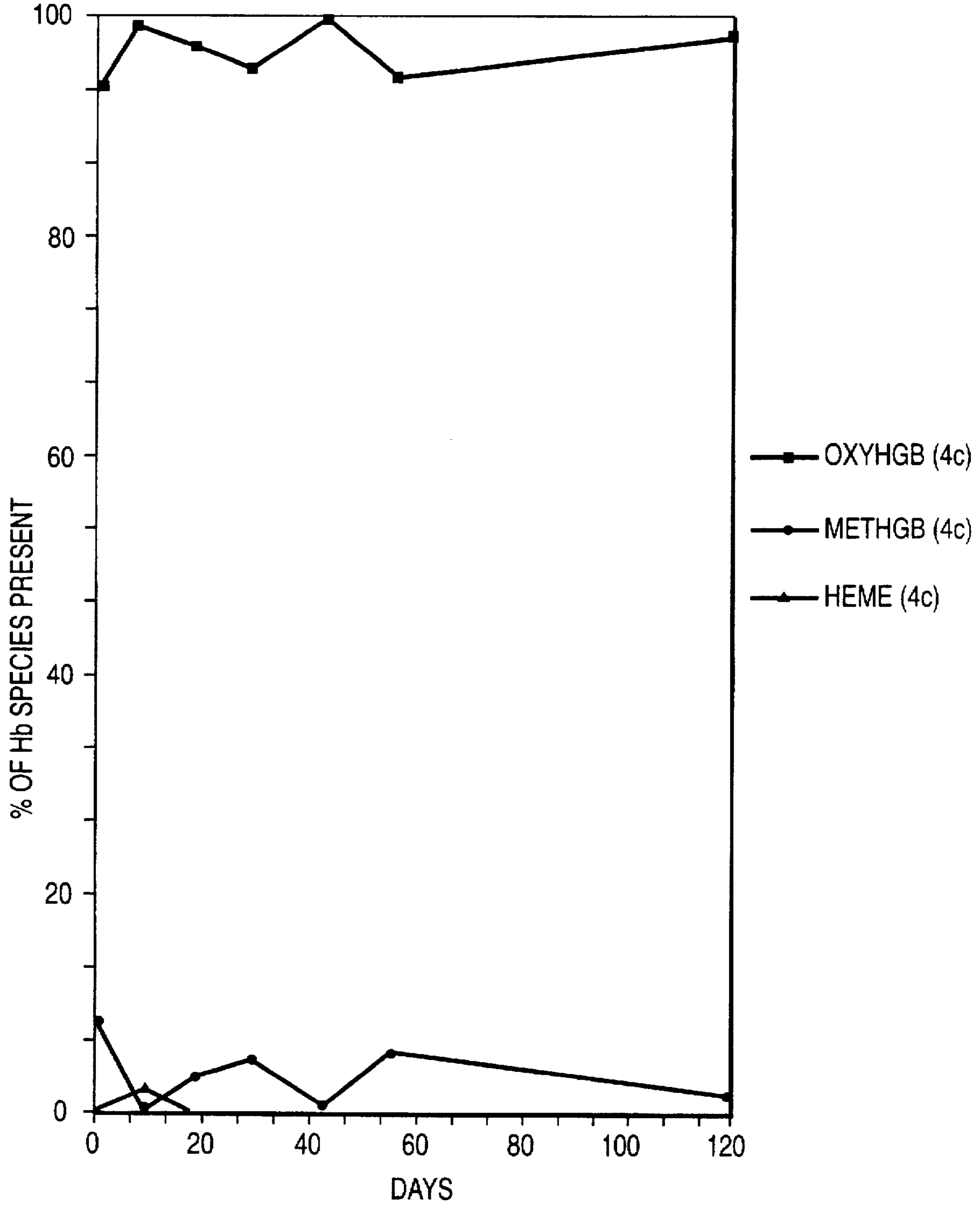
FIG. 3 is a plot of % Hb species present over time when lyophilized erythrocyte samples are stored at 4° C., then reconstituted after various storage times and assayed for oxyhemoglobin, methemoglobin, and hemichrome levels.
Figure 4:
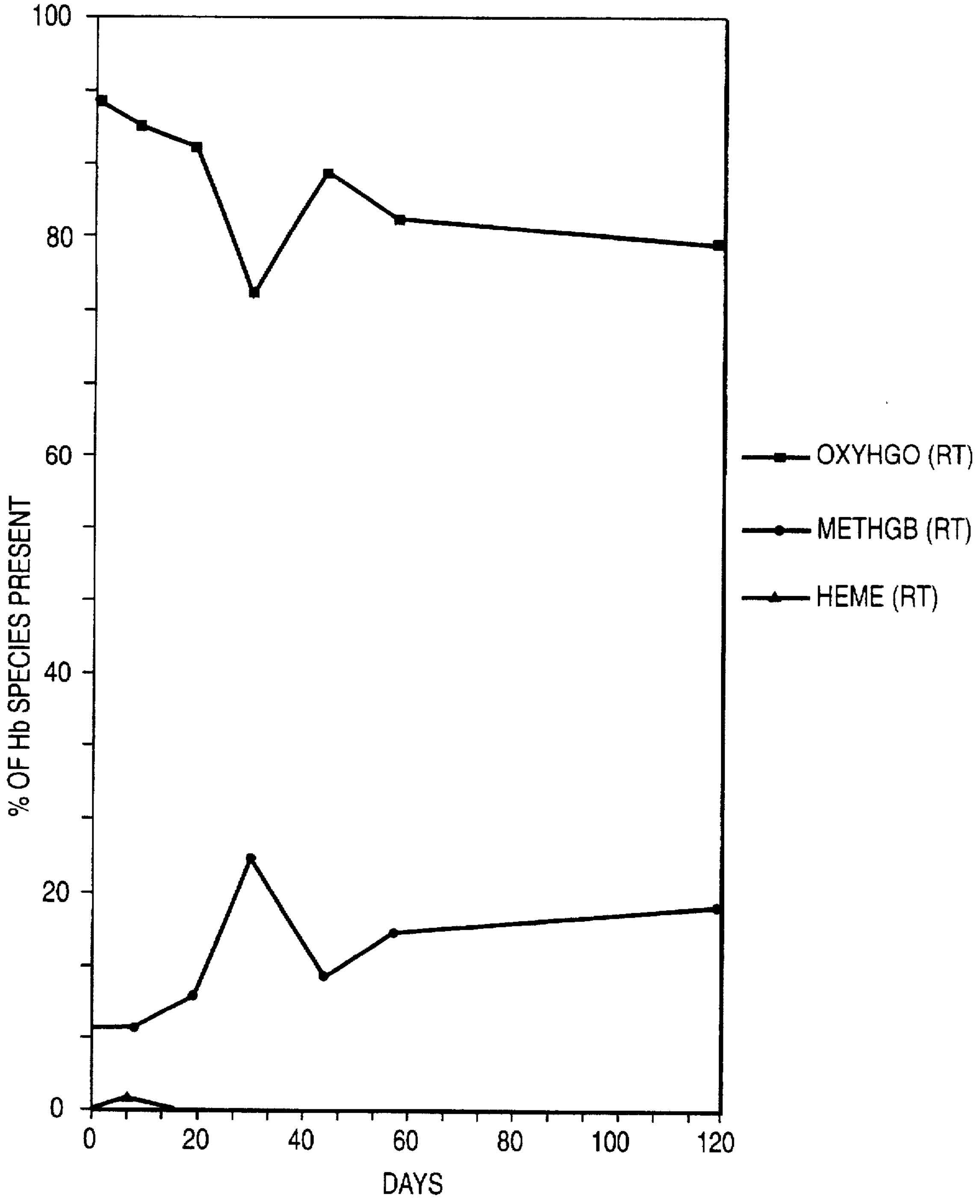
FIG. 4 is a plot of % Hb in lyophilized and reconstituted erythrocyte samples stored at room temperature for different periods of time.

To assess the effects of lyophilized storage at room temperature versus refrigerated, 6 ml samples of human red cells were lyophilized in 50 ml vials and stoppered under vacuum upon completion of the drying cycle. All samples were scored visually for dryness and the starting sample residual moisture was in the 2% range that we consistently achieve during shelf drying. Four samples were immediately reconstituted and analyzed to provide a time zero reference point, and the remaining vials were stored in the dark at either room temperature or refrigerated (4° C.). After 1,2, 4, 6, 8 and 17 weeks of storage, three vials maintained at each temperature were reconstituted and the recovered cells were pooled before analysis. The percent cell recovery, hemoglobin content, and red cell indices were then examined. The results are shown in FIGS. 2, 3 and 4. The level of methemoglobin increases at room temperature, but refrigerated storage inhibits methemoglobin formation.

Solid Phase Assays

Example 6

A 0.35% suspension of fresh human red blood cells in PBS was prepared by washing 1.0 ml fresh red blood cells in a 12×75 mm test tube three times with PBS. These red cells were prepared from volunteer whole blood collected in standard anticoagulants. The cells were resuspended and the hematocrit was determined. From the spun hematocrit reading, the dilution was determined, which was necessary to obtain 10 ml of a 0.35 suspension of cells. A sample of 50 microliters of a 0.35% suspension of red blood cells in PBS was added to all the test wells of two 96 well microplates, except for wells G&H of plate #2. The blank microplates are commercially available from Immucor Inc., Norcross, Georgia, and are designed to bind human red cells (Capture-R plate system). The plates were centrifuged at 1,000 rpm for 5 minutes. The excess unbound cells were removed by decanting, then the plates were washed 6 times with PBS.

To plate #1 the following were added:

rows A & B: 100 ul lyophilization buffer (80:20 with PBS).

rows C & D: 50 ul buffer (80:20 with PBS).

rows E & F: 100 ul lyophilization buffer (80:20 with 0.006% GDA).

rows G & H: 50 ul lyophilization buffer (80:20 with 0.006% GDA).

Add to plate #2:

rows A & B: 100 ul lyophilization buffer (80:20 with 0.024% GDA).

rows C & D: 75 ul lyophilization buffer (80:20 with 0.024% GDA).

rows E & F: 50 ul lyophilization buffer (80:20 with 0.024% GDA).

rows G: 100 ul lyophilization buffer (80:20 with 0.024% GDA).

row H: 50 ul lyophilization buffer (80:20 with 0.024% GDA).

PBS=phosphate buffered saline GDA =Glutaraldehyde

The plates were then centrifuged at 1000 rpm for 5 minutes, then lyophilized using a Virtis shelf model freeze-dryer. Aluminum plates were used to achieve good contact between the refrigerated shelf and the bottom of each microplate well. After the lyophilization cycle was complete, the dry plates were removed. Then 200 microliters of rehydration buffer was added to test rows A,C,E and G, and 200 microliters of 0.85% PBS was added to test well rows B,D,F and H. The plates were allowed to rehydrate for 20 minutes at room temperature. The rehydration solutions were removed by decanting, then the plates were washed 6 times with PBS. Then 50 microliters of a 0.35% suspension of red blood cells (from the same source as previously used) in PBS were added to test wells G & H of plate #2 and 50 microliters of PBS to all other wells. The plates were again centrifuged at 1000 rpm for 5 minutes. The excess unbound cells were removed by decanting, then the plate #2 was washed 6 times with PBS. Then to each plate was added as follows:

column 1: 50 ul of the strong control serum.

column 2: 50 ul of the weak control serum.

column 3: 50 ul of the negative control serum.

column 4: 50 ul of anti-D serum.

column 5: 50 ul of the anti-c serum.

column 6: 50 ul of the anti-M serum.

column 7: 50 ul of the anti-s serum.

column 8: 50 ul of anti-k serum.

column 9: 50 ul of anti-$Fy^a$ serum.

column 10: 50 ul of anti-$Jk^b$ serum.

column 11: 50 ul of anti-$Le^a$ serum.

column 12: 50 ul of anti-$P_1$ serum.

The antisera used are commercially available blood typing antisera, and can be pooled human antisera, pooled animal antisera or monoclonal antibodies, or mixed polyclonal and monoclonal sera. These reagents are sold by several companies: Ortho Diagnostic Systems, Inc., Baxter Diagnostics Inc., Immucor Inc., Gamma Biologicals Inc., and Organon Teknika. All of these sources and types of available typing antisera can be used with the present invention.

Figure 5:
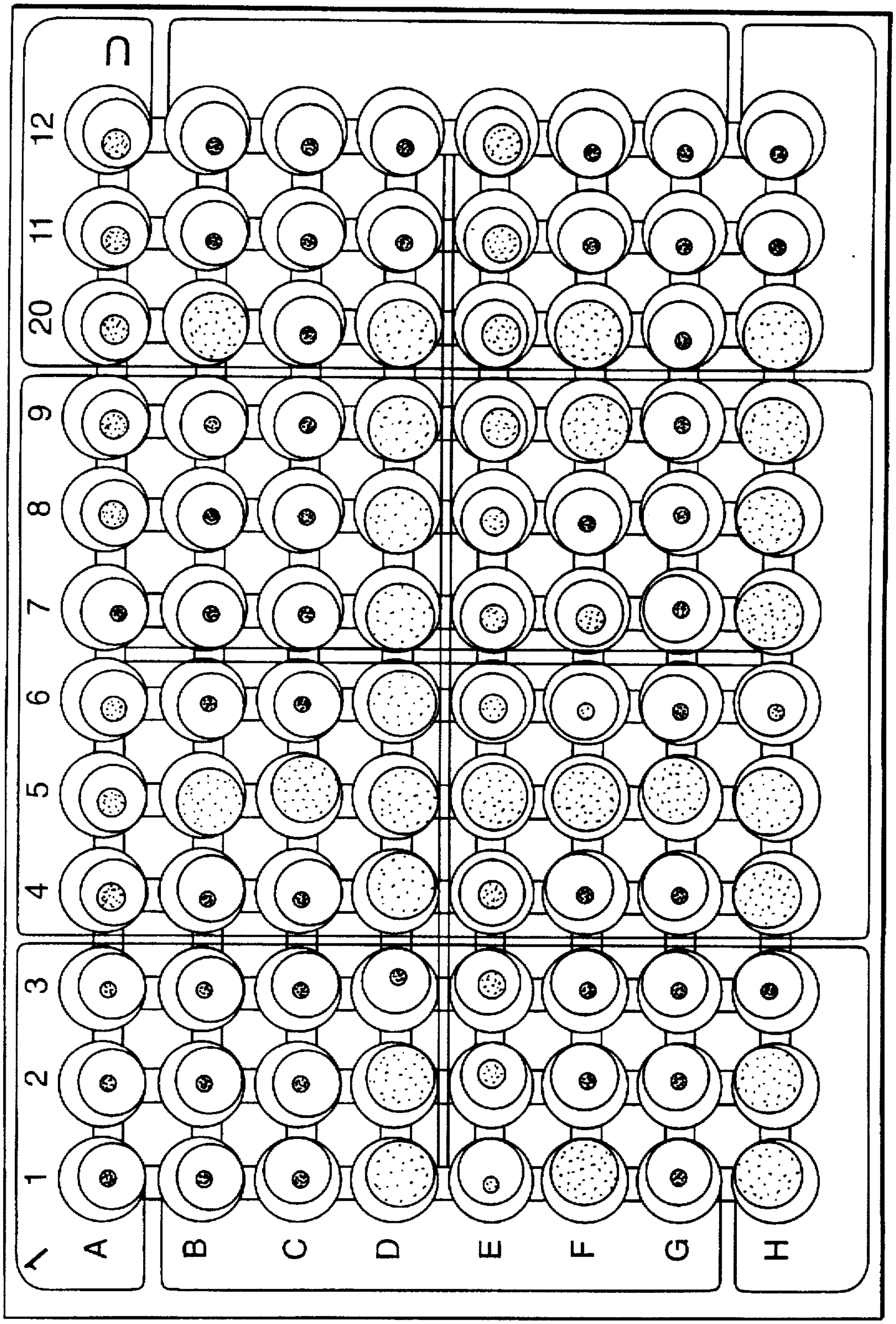
FIG. 5 is a photograph of a microplate, showing positive and negative results for a screening test for blood antibodies according to the present invention, whereby attached lyophilized cells are reconstituted in each well as a source of cell surface antigens. Adherence of sensitized red cells is used as the method to detect the presence or absence of bound antibodies.
Figure 6:
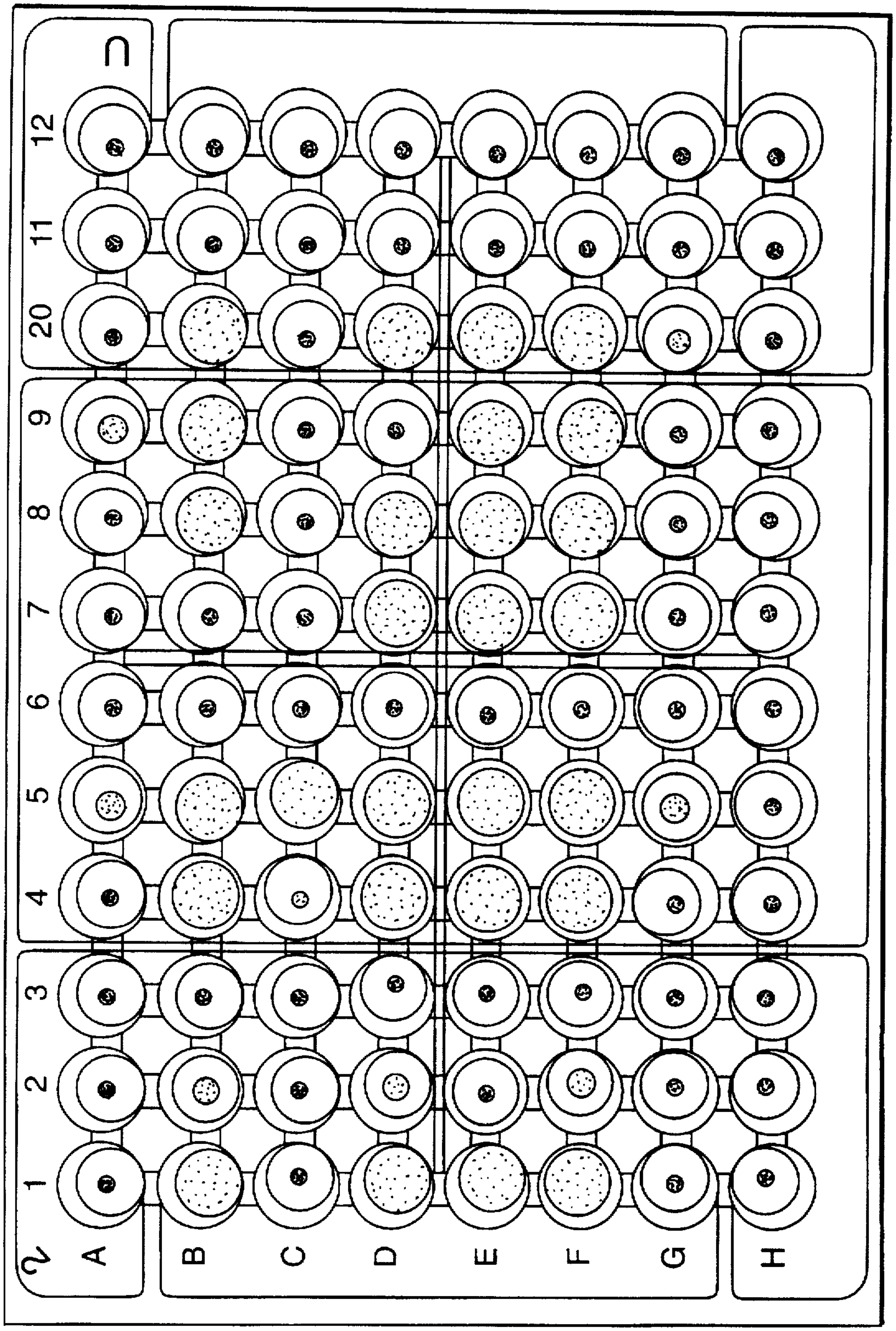
FIG. 6 is a second photograph of a microplate, showing a different set of positive and negative results for screening blood antibodies. Commercial sensitized red cells are used to detect bound antibodies.

Immediately thereafter, 100 microliters was added of LISS (Low Ionic Strength Saline) to each well. The plates were incubated at 36° to 38° C. no less than 15 minutes and no more than 60 minutes. The serum-LISS mixture was decanted from the plates, then the plates were washed 6 times with PBS. About 50 microliters of indicator red cells (Immucor Inc.) were added to each well. The plates were immediately centrifuged at 1600 rpm for 2 minutes. The plates were placed on an illuminated surface and examined for adherence or the absence of indicator cell adherence (button). A valid test must include a positive strong control reaction (an even thin layer of indicator red cells over the entire reaction surface), a positive weak control (adherence of indicator red cells over part or all of the reaction surface), and a negative control serum (tight button of indicator red cells at the bottom of the test wells with no area of adherence). The control sera are commercially available from Immucor Inc. Plate #1 is shown as FIG. 5 and plate #2 is shown as FIG. 6. Clear, positive and negative results are shown. In FIG. 5 rows D & H are comparable to standard liquid typing (agglutination) results for the same blood donor. In FIG. 6 rows B, D and F are comparable to standard liquid typing results for the same blood donor.

Example 7

A test on 3 Capture-R microplates was conducted wherein blood cells from a single typed donor were attached to each plate before lyophilization. The plates were prepared as described in Example 6. One plate (FIG. 7*a*) was reconstituted upon removal from the lyophilizer and promptly used to screen reagent antisera of known specificity. A second plate (FIG. 7*b*) was stored at 22° C. for 24 hours, then reconstituted and used to screen the same antisera. A third plate (FIG. 7*c*) was stored for 7 days at 22° C. following lyophilization, then used to screen the antisera. There were no significant differences among the results for the three plates, thus showing that dry storage at room temperature did not adversely affect the accuracy of the tests using the diagnostic plates containing lyophilized cells.

Example 8

Microtiter® Capture-R plates with attached red cells from a typed donor were prepared by lyophilization as described in Example 6. One plate (FIG. 8*a*) was reconstituted immediately after lyophilization; a second plate (FIG. 8*b*) was stored at 4° C. for 7 days, then reconstituted; a third plate (FIG. 8*c*) was stored at 22° C. for 7 days, then reconstituted; a fourth plate (FIG. 8*d*) was stored at 4° C. for 14 days, then reconstituted; and a fifth plate (FIG. 8*e*) was stored at 22° C. for 14 days, then reconstituted. All plates were tested using commercial antisera of known specificity. Although there was some deviation of results attributed to the inconsistent quality of the plates, the consistency of results among the plates indicated that storage at 4° C. or 22° C. for 7 to 14 days did not significantly deteriorate the usefulness of the plates.

Example 9

Plates are prepared using fresh whole human blood collected from volunteer donors whose tissue (HLA) antigen type has been determined independently using the commercial microlymphocytotoxicity assay (Terasaki, 1964) available from One Lambda, Inc. Platelets are isolated from the anticoagulated whole blood. In Table 10 shows the HLA types of our donors (donors #003, 009, 017, 019, 026) determined by the One Lambda assay. Each person has two copies of the HLA-A and HLA-B genetic loci, hence a person can have one or two HLA-A and HLA-B phenotypes (a person with one phenotype may be homozygous for that locus). Thus, donor #003 is positive for both HLA-A1 and HLA-A10 (i.e., is heterozygous at the HLA-A locus). Donor #026 is only positive for HLA-A2 and HLA-B35, and may be homozygous at both loci. In addition, the majority of persons carry so-called "public" or common antigens, such as Bw4 and Bw6.

In this example the tests used a control of non-lyophilized fresh platelets pooled from four different donors and attached onto microplates (no exposure to lyophilization buffer occurred in these fresh controls). The attached platelet monolayers were reacted with commercial human anti-HLA-A1, anti-HLA-B5, and anti-M (a red cell antigen). Commercial positive anti-platelet control serum and negative control serum were used (Immucor Corp). As further controls, some wells received 4% BSA or plain PBS instead of antiserum. The antisera binding was then assayed using either commercial indicator red cells (Immucor) or those made by attaching anti-human IgG. The results clearly show detection of the presence of HLA-A1 antigen in the pooled platelets (from donors 003 and 017). There is no detection of HLA-B5, which is not found in any of the four donors by the microlymphocytotoxicity assay.

I. Red Cell Indicator System.

A. Procedure for non-lyophilized assay system:

1. Dispense 300 μl 0.25% glutaraldenhyde into the test wells of a round bottom microplate.
2. Incubate the microplate at room temperature for one hour.
3. Wash the microplate six times with 0.18M phosphate buffered saline (PBS).
4. Invert the microplate and drain for five minutes.
5. Dispense 100 μl platelet suspension into each test well.
6. Tightly wrap the microplate with parafilm and store at +4° C. overnight.
7. Remove the microplate for storage and bring to room temperature.
8. Wash the microplate once with PBS.
9. Dispense 300 μl 1% bovine serum albumin (BSA) into each test well.
10. Incubate the microplate at room temperature for one hour.
11. Wash the microplate three times with PBS.
12. Dispense 100 μl Low Ionic Strength Saline (LISS) into Qach test well.
13. Dispense 50 μl specific antiserum into the test well.
14. Incubate the microplate at 37°°C. for 30 minutes.
15. Wash the microplate three times with PBS.
16. Dispense 50 μl of Indicator red cells into each test well.
17. Centrifuge the microplate at 500×G for 3 minutes.
18. Observe the test well reactions of adherence of the indicator cells; positive reactions adhere forming an event monolayer of red cells, negative reactions do not adhere, thus forming a button of red cells at the bottom of the well.

TABLE 10

MICROLYMPHOCYTOTOXICITY PROFILES OF BLOOD DONORS
Platelet Source HLA Antigrams

| Source | HLA-A antigens | | HLA-B antigens | | Bw4 | Bw6 |
|---|---|---|---|---|---|---|
| 003 | 1 | 10 | 8 | 67 | + | + |
| 009 | 2 | – | 7 | 27 | + | + |
| 017 | 1 | 3 | 17 | 44 | + | – |
| 019 | 29/30 | – | 37 | 44 | + | – |
| 026 | 2 | – | 35 | – | – | + |

TABLE 11

Non-lyophilized pooled Platelets (003, 009, 017, & 019) with Indicator Red Cells

| | + control | – control | 4% BSA | PBS | A1 | B5 | M |
|---|---|---|---|---|---|---|---|
| expected reactions | + | – | – | – | + | – | – |
| Immucor Ind. red cells | + | –/+ | –/+ | –/+ | + | + | – |
| Cryopharm | | | | | | | 00 |
| Ind. red cells | + | – | – | – | + | – | – |

+ = positive reaction; – = negative reaction; +/– = positive reaction, but some Indicator cells not forming a monolayer; –/+ = weak reaction, but tight button not formed;

Example 10

Lyophilized microplates are prepared using pooled platelets from three donors, and as in Example 9. There was no detection of HLA-A11 antigen, as expected since none of these donors was positive for A11. Again, the presumed red cell-specific antigen M was not detected using commercial antisera against these antigens. The results demonstrate the use of indicated red cells. Positive reactions are evidenced by a smear of adhered red indicated cells, while negative reactions form a pellet or "button" at the bottom of each U-bottomed well after centrifugation.

B. Procedure for lyophilized assay system:

1. Dispense 300 μl 0.25% glutaraldehyde into the test wells of around bottom microplate.
2. Incubate the microplate at room temperature for one hour.
3. Wash the microplate six times with 0.18M phosphate buffered saline (PBS).
4. Invert the microplate and drain for five minutes.
5. Dispense 100 μl plateler suspension into each test well.
6. Tightly wrap the microplate with parafilm and store at +4° C. overnight.
7. Remove the microplate for storage and bring to room temperature.
8. Wash the microplate once with PBS.
9. Dispense 300 μl 1% bovine serum albumin (BSA) into each test well.
10. Incubate the microplate at room temperature for one hour.
11. Wash the microplate three times with PBS.
12. Dispense 50 μl of lyophilization buffer into each test well.
13. Place the microplate onto an aluminum planchet on the lyophilizer shelf (preset at –60° C.).

14. Freeze the microplate for one hour prior to initiating lyophilization cycle.
15. Remove the microplate from the lyophilzer.
16. Dispense 200 μl PBS into each test well.
17. Incubate the microplate at room temperature for 5 minutes.
18. Wash the microplate three times with PBS.
19. Dispense 100 μl Low Ionic Strength Saline (LISS) into each test well.
20. Dispense 50 μl specific antiserum into the test well.
21. Incubate the microplate at 37° C. for 30 minutes.
22. Wash the microplate three times with PBS.
23. Dispense 50 μl of Indicator red cells into each test well.
24. Centrifuge the microplate at 500×G for 3 minutes.
25. Observe the test well reactions of adherence of the indicator cells; positive reactions adhere forming an even monolayer of red cells, negative reactions do not adhere, thus forming a button of red cells at the bottom of the well.

TABLE 12

| Lyophilized pooled Platelets (003, 009, & 019) with Indicator Red Cells | | | | | | | |
|---|---|---|---|---|---|---|---|
| | + control | − control | 4% BSA | PBS | A1 | A11 | M |
| expected reactions | + | − | − | − | + | − | − |
| Cryopharm Ind. red cells | + | − | − | − | + | − | − |

Example 11

An enzyme-linked immunoassay is used based on horseradish peroxidase conjugated anti-human IgG (HRP-IgG) with lyophilized microplates containing dry platelets from three donors (#003, 009, 019). In both Examples 10 and 11 the lyophilization buffer recipe is 12% (w/v) 40,000 molecular weight PVP, 0.6 M glucose in 0.18 M phosphate buffered saline, pH 7.4. Note that a detergent wash in Tween 20 is needed to remove non-specifically bound HRP-IgG prior to addition of the chromogenic substrate (see protocol). The color reagent TMB plus hydrogen peroxide then forms a deep blue color if attached HRP-IgG is present. Negative wells remain clear (i.e., appear as clear as water).

II. ELISA System.

Procedure for lyophilized assay system:

1. Dispense 300 μl 0.25% glutaraldehyde into the rest wells of a round bottom microplate.
2. Incubate the microplate at room temperature for one hour.
3. Wash the microplate six times with 0.18 M phosphate buffered saline (PBS).
4. Invert the microplate and drain for five minutes.
5. Dispense 100 μl platelet suspension into each test well.
6. Tightly wrap the microplate with parafilm and store at +4° C. overnight.
7. Remove the microplate for storage and bring to room temperature.
8. Wash the microplate once with PBS.
9. Dispense 300 μl 1% bovine serum albumin (BSA) into each test well.

10. Incubate the microplate at room temperature for one hour.
11. Wash the microplate three times with PBS.
12. Dispense 50 μl of lyophilization buffer into each test well.
13. Place the microplate onto an aluminum planchet on the lyophilizer shelf (preset at −60° C.).
14. Freeze the microplate for one hour prior to initiating lyophilization cycle.
15. Remove the microplate from the lyophilzer.
16. Dispense 200μl PBS into each test well.
17. Incubate the microplate at room temperature for 5 minutes.
18. Wash the microplate three times with PBS.
19. Dispense 100 μl Low Ionic Strength Saline (LISS) into each test well.
20. Dispense 50 μl specific antiserum into the test well.
21. Incubate the microplate at 37° C. for 30 minutes to 90 minutes.
22. Wash the microplate three times with PBS.
23. Dispense 150 μl of IgG-HRP conjugate into each test well.
24. Incubate the microplate at room temperature for 30 minutes.
25. Wash the microplate three times with 0.05% Tween 20 in PBS (PT20).
26. Dispense 150 μl TMB: $H_2O_2$ solution into each test well.
27. Incubate the microplate at room temperature for 15 minutes.
28. Read the absorbance of the reactions at 630 nm.
29. Dispense 150 μl 2N $H_3PO_4$ into each test well to stop the reaction.
30. Read the absorbance of the reactions at 450 nm.

TABLE 13

| Lyophilized pooled Platelets (003, 009, * 019) with HRP - TMB indicator system | | | | |
|---|---|---|---|---|
| | + control | 4% BSA | PBS | A1 |
| expected reactions | + | − | − | + |
| 40K PVP + glucose in PBS | + | − | − | + |

HRP = horseradish peroxidase
TMB = 3,3',5,5'-tetramethylbenzidine
+ = color detected by visual inspection
− = no color; well remained clear Note: in Examples 10 and 11 the lyophilization buffer used was:

12% (w/v) 40K PVP
0.6M Glucose
0.18M phosphate buffered saline,
pH 7.4

Example 12

Polystyrene antibody-coated beads are used as indicators to detect the presence of bound serum antibodies in lyophilized red blood cell disgnostic microplates.

The data in Table 14 show that synthetic beads ranging from 3–12 micron average diameter can be coated with anti-human IgG and used with freeze-dried red cell microplate to detect binding of red cell antibodies in the control antisera. Different centrifugation speeds to pellet the beads (akin to using indicator antibody coated red cells) and bead titer were also evaluated. In the data table, Pos=Immucor positive control antiserum, Weak=Immucor weak positive control antiserum, Neg=Immucor negative control antiserum, adn NSB=nonspecific binding control where PBS is substituted for antiserum.

These data demonstrate the use of immunobead indicator methods in combination with freeze-dried, rehydrated red cell microplates.

POLYSTYRENE INDICATORS

TYPICAL FORMULATION:

1. Transfer 1 ml of a 2.5% suspension of beads (Polysciences, Inc. Warrington, Pa.) into an Eppendorf tube (1.9 ml).
2. Fill the tube with 0.1 M PBS pH 7.4 and cap
3. Centrifuge for 5 minutes at 3500 rpm in an Eppendorf 2150 microfuge
4. Remove supernatant with a pastuer pipette and discard supernatant.
5. Fill tube with PBS as above, cap tube and resuspend the beads using a vortex mixer.
6. Centrifuge as above in step 3.
7. Wash two additional times by repeating steps 4.5 and 6 twice.
8. Resuspend the pellet in 1 ml of 8% glutaraldehyde (25% E grade) in 0.1 M PBS pH 7.4
9. Incubate overnight at room temperature with rocking.
10. Centrifuge for 5 minutes at 3500 rpm as above in step 3.
11. Wash the pellet three times in PBS as above in steps 4.5, and 6.
12. Resuspend the beads in 1 ml of 0.1M PBS pH 7.6 and add 400 mg of anti-human IgG.
13. Incubate at room temperature overnight with rockign.
14. Centrifuge at 10 minutes at 5000 rpm in an Eppendorf 2150 microfuge.
15. Remove supernatant and perform protein determination to determine binding efficiency.
16. Resuspend the pellet in 1 mL of 2% BSA in 0.1M PBS pH 7.6.
17. Incubate for 2 hours at room temperature with rocking.
18. Centrifuge for 5 minutes at 35000 rpm as above in step 3.
19. Resuspend in 0.1% BSA in 0.1M PBS pH 7.6 and store at 2° to 80° C. Titer appropriately for use.

TABLE 14

| Particle Size | RCF | Titer | Pos + | Weak +/− | Neg − | NSB − |
|---|---|---|---|---|---|---|
| 3.0 micron | 1500 | 0.25% | + | +/− | − | − |
| 4.5 micron | 1500 | 0.25% | + | +/− | − | − |
| 6.0 micron | 1300 | 0.25% | + | +/− | − | − |
| 6.0 micron yellow | 1300 | 0.15% | + | +/− | − | − |
| 12.0 micron | 1000 | 0.15% | + | +/− | − | − |

Assay Conditions:

1. Lyophilized rounded bottom microwell plates with RBCs attached were rehydrated by adding 200 microliters of Dubecco's PBS and allowing to incubate for 20 minutes at room temperature.
2. The plates were subsequently washed 3 times with Dulbeccos, inverted and banged once on a paper towel to remove any residual buffer droplets.
3. 50 microliters of the appropriate antisera was added to its designated well.
2. 100 microliters of LSS was added to all wells and incubated for thirty (30) minutes at 37° C.
3. The plates were washed three (3) times with Dulbecco's PBS.
4. 50 microliters of the pretitered particles were added to all wells.
5. The plate was centrifuge for 3 minutes at the appropriate RCF.
6. The plate was inspected and the results interpretted.

Experimental conditions:

An assay using anti-human IgG coated particles was compared to an assay using anti-human IgG coated indicator cells and the results were compared.

PLATE PREPARATION

1. Add 200 microliters of Dulbeccos PBS to all wells of the plate (Corning high binding microplates) and allowed to incubate for 1 hour at 37° C.
2. The plates are emptied.
3. 200 microliteres of 0.12% GDA in Dulbeccos PBS is added to all wells and the plates are incubated for 1 hour at room temperature.
4. The plates are emptied and 100 microliter of RBCs (0.35% in Dulbeccos containing 0.12% GDA) is added to all wells.
5. The plates are centrifuged at 800×G for 5 minutes.
6. The plates are washed three times with Dulbeccos
7. The plates are dunked into a 0.15% GDA in Dulbeccos at 4° C. for 5 minutes.
8. The plates are washed three times.
9. 50 Microliters of lyo buffer is added to all the wells
10. The plates are lyophilized using the standard 24 hour lyophilization protocol.

Lyobuffer

12% (w/v) 40K PVP 0.6 M Glucose 0.18 M PBS pH 7.4

Controls and indicators are from Immucor Corp. Norcross Ga.

What is claimed is:

1. A method of forming dry cells, cell membranes, lymphocytes, platelets, peripheral blood cells, stem cells, liposomes, hemosomes, cell membrane ghosts, cultured mammalian cells, stroma, hybridoma cells or erythrocytes, bound to a solid support comprising the steps of:

(a) binding a material selected from the group consisting of cells, cell membranes, lymphocytes, platelets peripheral blood cells, stem cells, liposomes, hemosomes, cell membrane ghosts, cultured mammalian cells, stroma, hybridoma cells and erythrocytes, having a profile of cytosolic or cell surface receptors capable of being recognized and bound by a ligand, to said solid support;

(b) immersing the bound material in a cryoprotective medium comprising a carbohydrate selected from the group consisting of a monosaccharide, a disaccharide and a trisaccharide and at least one biologically compatible amphipathic polymer; and ⓒ lyophilizing said bound material and cryoprotective medium to form a lyophilized composition.

2. A method for forming dry cells, cell membranes, lymphocytes, platelets, peripheral blood cells, stem cells, liposomes, hemosomes, cell membrane ghosts, cultured mammalian cells, stroma, hybridoma cells or erythrocytes, bound to a solid support comprising the steps of:

(a) binding a material selected from the group consisting of cells, cell membranes, lymphocytes, platelets, peripheral blood cells, stem cells, liposomes, hemosomes, cell membrane ghosts, cultured mammalian cells, stroma, hybridoma cells and erithrocytes, having a profile of cytosolic or cell surface receptors capable of being recognized and bound by a ligand, to a solid support;

(b) immersing the bound cells, cell membranes, lymphocytes, platelets, peripheral blood cells, stem cells, liposomes, hemosomes, cell membrane ghosts, cultured mammalian cells, stroma, hybridoma cells or erythrocytes in a cryoprotective medium comprising a carbohydrate selected from the group consisting of a monosaccharide, a disaccharide and a trisaccharide and at least one biologically compatible amphipathic polymer; and ⓒ evaporatively drying said bound material and cryoprotective medium to form a dried composition.

3. A method of detecting in vitro the presence or absence of a ligand in a fluid sample comprising the steps of:

(a) binding a material selected from the group consisting of cells, cell membranes, lymphocotes, platelets, peripheral blood cells, stem cells, liposomes, hemosomes, cell membrane ghosts, cultured mammalian cells, stroma, hybridoma cells and erythrocytes having a profile of cytosolic or cell surface receptors capable of being recognized and bound by said ligand, to a solid support;

(b) immersing the bound cells, cell membranes, lymphocytes, platelets, peripheral blood cells, stem cells, liposomes, hemosomes, cell membrane ghosts, cultured mammalian cells, stroma, hybridoma cells or erythrocytes in a cryoprotective medium comprising a carbohydrate selected from the group consisting of a monosaccharide, a disaccharide and a trisaccharide and at least one biologically compatible amphipathic polymer;

ⓒ lyophilizing said bound material and cryoprotective medium;

(d) reconstituting the lyophilized material;

(e) optionally, washing the reconstituted material;

(f) contacting said reconstituted material with a fluid sample containing or suspected of containing said ligand; and (g) detecting the presence or absence of ligand bound to said receptors.

4. A method of detecting in vitro the presence or absence of a ligand in a fluid sample comprising the steps of:

(a) binding a material selected from the group consisting of cells, cell membranes, lymphocytes, platelets, peripheral blood cells, stem cells, liposomes, hemosomes, cell membrane ghosts, cultured mammalian cells, stroma, hybridoma cells and erythrocytes, having a profile of cytosolic or cell surface receptors capable of being recognized and bound by said ligand to a solid support;

(b) immersing the bound material in a cryoprotective medium comprising a carbohydrate selected from the group consisting of a monosaccharide, a disaccharide and a trisaccharide and at least one biologically compatible amphipathic polymer;

ⓒ evaporatively drying said bound material and cryoprotective medium;

(d) reconstituting the dried material;

(e) optionally, washing the reconstituted material;

(f) contacting said reconstituted material with a fluid sample containing or suspected of containing said ligand; and (g) detecting the presence or absence of ligand bound to said receptors.

5. A method according to claim 3 or 4 wherein, prior to said reconstituting of material in step (d) the dried or lyophilized material from step (c) is stored.

6. A method of detecting in vitro the presence or absence of a ligand in a sample fluid comprising the steps of (a) reconstituting a lyophilized composition, said composition comprising a material selected from the group consisting of cells, cell membranes, lymphocytes, platelets, peripheral blood cells, stem cells, liposomes, hemosomes, cell membrane ghosts, cultured mammalian cells, stroma, hybridoma cells and erythrocytes lyophilized or dried in the presence of a cryoprotectant comprising a monosaccharide, a disaccharide or a trisaccharide and at least one biologically compatible amphipathic polymer and known to have a profile of cytosolic or cell surface receptors which are recognized and bound by said ligand;

(b) optionally, washing the reconstituted composition from step (a);

ⓒ contacting said reconstituted composition with said sample; and (d) detecting the presence or absence of ligand bound to said receptors.

7. A method of detecting in vitro the presence or absence of a ligand in a sample fluid comprising the steps of:

(a) reconstituting a dried composition, said composition comprising a material selected from the group consisting of cells, cell membranes, lymphocytes, platelets, peripheral blood cells, stem cells, liposomes, hemosomes, cell membrane ghosts, cultured mammalian cells, stroma, hybridoma cells and erythrocytes lyophilized or dried in the presence of a cryoprotectant comprising a monosaccharide, a disaccharide or a trisaccharide and at least one biologically compatible amphipathic polymer and known to have a profile of cytosolic or cell surface receptors which are recognized and bound by said ligand;

(b) optionally, washing the reconstituted composition from step (a);

ⓒ contacting said reconstituted composition with said sample; and (d) detecting the presence or absence of ligand bound to said receptors.

8. A method according any of claim 3, 4, 6 or 7 wherein said sample is selected from the group consisting of plasma, serum, antiserum, hybridoma fluid, tissue or body fluids, cell culture fluids, whole blood, and fractions derived from tissue or body fluids, cell culture fluids, whole blood, plasma, serum, antiserum, or hybridoma fluid.

9. A method according to any of claims 1, 2, 3, 4, 6 or 7 wherein said ligand is a circulating antibody.

10. A method according to claim 9 wherein said receptors comprise cell-surface antigens.

11. A method according to claim 6 wherein a plurality of separate compositions is reconstituted; optionally washed, and each is separately mixed with a sample selected from the group consisting of plasma and serum, thereby providing a panel of standard compositions for screenings a predetermined set of ligands.

12. A method according to any of claims 1, 2, 3, 4, 6 or 7 wherein said cells are selected from the group consisting of tissue samples, cultured cells, stem cells, peripheral blood cells, and cancer cells.

13. A method according to any of claims 1, 2, 3, 4, 6 or 7 wherein said cells are selected from the group consisting of erythrocytes, lymphocytes, platelets, liposomes and hemosomes.

14. A method according to claims 1, 2, 3, 4, 6 or 7 wherein said cells are treated with activating agents that enhance receptor-ligand binding or increase the expression of cell receptors.

15. A method according to claim 14 wherein said activating agents are selected from the group consisting of digestive enzymes, cell growth factors, proteases, glycohydrolases, and cell maturation and differentiation factors.

16. A method according to claim 15 wherein said proteases are selected from the group consisting of bromelain, papain, trypsin, chymotrypsin, pronase, ficin and proteinase K.

17. A method according to any of claims 3, 4, 6 or 7 wherein said ligand is a steroid hormone.

18. A method according to any of claims 3, 4, 6 or 7 wherein said ligand is a growth factor.

19. A method according to any of claims 3, 4, 6 or 7 wherein said ligand is a protein or peptide.

20. A method according to any of claims 3, 4, 6 or 7 wherein said ligand is a metabolite.

21. A method according to claim 20 wherein said metabolite is an inorganic or organic compound.

22. A method according to claim 21 wherein said inorganic or organic compounds are selected from the group consisting of trace elements, cofactors, cyclic nucleosides, toxins, pharmaceutical drugs, nucleic acids, and metabolic byproducts of toxins and pharmaceutical drugs.

23. A method according to any of claims 1, 2, 3, 4, 6 or 7 wherein said cytosolic receptors are selected from the group consisting of cell enzymes and intracellular receptors.

24. A method according to claim 23 wherein said intracellular receptors comprise steroid hormone receptors.

25. A method according to claim 6 or 7 wherein said lyophilized or dried composition further comprises an enhancer for enhancing a desired ligand-receptor reaction.

26. A method according to claim 25 wherein said enhancer comprises a polymer.

27. A method according to claim 26 wherein said polymer comprises polyethylene glycol.

28. A method according to claim 25 wherein said enhancer comprises a protein.

29. A method according to claim 28 wherein said protein comprises bovine serum albumin.

30. A method according to claim 28 wherein said protein comprises an enzyme.

31. A method according to claim 30 wherein said enzyme is a protease or glycohydrolase.

32. A method according to claim 25 wherein said enhancer imparts to said composition, when reconstituted, a pH of about 7.2 or lower.

33. A method according to any of claims 3, 4, 6 or 7 wherein said material comprises erythrocytes.

34. A method according to any of claims 3, 4, 6 or 7 wherein said material comprises platelets.

35. A method according to any of claims 3, 4, 6 or 7 wherein said composition material comprises lymphocytes.

36. A method according to any of claims 3, 4, 6 or 7 wherein said composition material comprises liposomes.

37. A method according to any of claims 3, 4, 6 or 7 wherein said material comprises hemosomes.

38. A method according to any of claims 3, 4, 6 or 7 wherein said material comprises peripheral blood cells.

39. A method according to any of claims 3, 4, 6 or 7 wherein said material comprises stem cells.

40. A method according to any of claims 3, 4, 6 or 7 wherein said material comprises cancer cells.

41. A method according to any of claims 3, 4, 6 or 7 wherein said material comprises tissue explants.

42. A method according to any of claims 3, 4, 6 or 7 wherein said sample fluid is selected from the group consisting of human plasma and serum.

43. A method according to any of claims 3, 4, 6 or 7 wherein said sample fluid is selected from the group consisting of animal plasma and serum.

44. A method according to any of claims 1, 2, 3, 4, 6 or 7 wherein said material comprises human cells.

45. A method according to any of claims 1, 2, 3, 4, 6 or 7 wherein said [composition] material comprises animal cells.

46. A method as claimed in claim 45 wherein said animal cells are mammalian cells.

47. A method according to any of claims 1, 2, 3, 4, 6 or 7 wherein said material comprises antibody-coated cells.

48. A method as claimed in claim 47 wherein said antibodycoated cells are antibody-coated erythrocytes.

49. A method according to claim 48 wherein said antibody is selected from the group consisting of antihuman IgG and antihuman IgM.

50. A method according to claim 47 wherein said antibody-coated cells are selected from the group consisting of non-human mammalian cells and human cells.

51. A method according to claim 47 wherein said antibody-coated cells comprise fluorescently tagged antibodies.

52. A method according to claim 51 wherein said antibodies are derived from polyclonal antisera.

53. A method according to claim 51 wherein said antibodies are derived from hybridoma cell cultures.

54. A method according to any of claims 1, 2, 3, 4, 6 or 7 wherein said material comprises cellular membranes.

55. A method according to claim 54 wherein said membranes are mammalian cell membranes.

56. A method according to claim 55 wherein said cell membranes are selected from the group consisting of membranes prepared from erythrocytes, lymphocytes, platelets, peripheral blood cells, stem cells, cancer cells and tissue explants.

57. A method according to any of claims 1, 2, 3 or 4 wherein a plurality of separate compositions is lyophilized- or dried while attached to a solid support, thereby providing a panel of standard compositions for screening a predetermined set of antibody types.

58. A method according to claim 57 wherein said standard composition is selected from the group consisting of cell membranes, cell membrane fragments, and cell membrane ghosts.

59. A method according to claim 57 wherein said standard composition is selected from the group consisting of leukocytes, platelets, lymphocytes, and red blood cells.

60. A method according to claim 57 wherein said standard composition is selected from the group consisting of peripheral blood cells and hematopoietic stem cells.

61. A method according to claim 57 wherein said standard composition is mammalian cells.

62. A method according to claim 57 wherein said standard composition is selected from the group consisting of cancerous cultured cell lines and primary tumor cell explants.

63. A method according to claim 57 wherein said standard composition comprises cultured nerve cells.

64. A method according to claim 57 wherein said sample composition is animal antisera.

65. A method according to claim 57 wherein said sample composition comprises hybridoma cell fluid.

66. A method according to any of claims 3,4, 6 or 7 wherein said detecting of bound ligands comprises use of an agent selected from the group consisting of secondary antibodies and antibody-conjugates.

67. A method according to claim 66 wherein said use comprises an immunoassay selected from the group consisting of indirect immunoassays and competitive immunoassays.

68. A method according to claim 67 wherein said agent is attached to a solid support.

69. A method according to claim 68 wherein said solid support is selected from the group consisting of pellets, beads, and microspheres.

70. A method according to claim 69 wherein said solid support comprises a material selected from the group consisting of natural or synthetic polymers, and glass.

71. A method according to claim 70 wherein said polymers are selected from the group consisting of agar, agar derivatives, gelatin, plastics, cellulose, and latex.

72. A method according to claim 66 wherein said secondary antibodies are selected from the group consisting of antibodies directed against IgG and antibodies directed against IgM.

73. A method according to claim 66 wherein said secondary antibodies comprise anti-human antibodies.

74. A method according to claim 66 wherein said antibody-conjugates comprise antibody-radioisotope conjugates.

75. A method according to claim 74 wherein said radioisotopes are selected from the group consisting of $^{125}I$, $^{131}I$, $^{3}H$, $^{14}C$, and $^{35}S$.

76. A method according to claim 66 wherein said antibody conjugates comprise antibody-enzyme conjugates.

77. A method according to claim 76 wherein said antibody-enzyme conjugates are selected from the group consisting of alkaline phosphatase, horseradish peroxidase, beta-D-galactosidase, and glucose oxidase.

78. A method according to claim 66 wherein said conjugates compromise antibodies conjugated with fluorochrome dyes.

79. A method according to claim 78 wherein said fluorochrome dyes are selected from the group consisting of rhodamine, fluorescein, and phycobiliproteins.

80. A method according to any of claims 3, 4, 6 or 7 wherein said detecting of bound ligand comprises measurement of altered optical properties in the reaction solution.

81. A method according to claim 80 wherein said optical properties are selected from the group consisting of light scatter, light reflection, light transmission, and optical density.

82. A method according to any of claims, 3, 4, 6 or 7 wherein said detecting comprises immunoglobulin binding proteins.

83. A method according to claim 82 wherein said immunoglobulin-binding protein is selected from the group consisting of Protein A, Protein G, and antibodies.

84. A method according to claim 83 wherein said immunoglobulin-binding protein is selected from recombinant proteins, polyclonal antibodies, and monoclonal antibodies.

85. A method according to any of claims 3, 4, 6, or 7 wherein said ligand is selected from the group consisting of biotin or biotin-conjugated proteins and nucleic acids.

86. A method according to claims 3, 4, 6 or 7 wherein said ligand is selected from the group consisting of avidin or conjugates of avidin with enzymes, fluorescent dyes, colloidal gold particles and metals.

87. A method according to any of claims 3, 4, 6 or 7 wherein said detecting is selected from the group consisting of an enzyme-linked immunosorbent assay, radioimmunoassay, enzyme immunoassay, and competitive immunoassay.

88. A method according to any of claims 3, 4, 6, or 7 wherein said detecting comprises an agglutination assay.

89. A method according to claim 88 wherein said agglutination assay comprises agglutination of cells.

90. A method accordingto claim 88 wherein said ahhlutination assay comprises agglutination of a material selected from the group consisting of cell-like materials, beads, particles, and microspheres.

91. A method according to claim 90 wherein said cells, beads, particles, or microspheres are treated with immunoglobulin-binding proteins.

92. A method acceding to claim 91 wherein said immunoglobulin-binding proteins are selected from the group consisting of Protein A, Protein G, and antibodies.

93. A method according to any of claims, 3, 4, 6 or 7 wherein said detecting comprises red cell adherence of antibody coated indicator red blood cells.

94. A method according to claim 89 wherein said cells comprise red blood cells.

95. A method according to claim 94 wherein said red blood cells comprise antibody-coated red blood cells.

96. A method according to claim 96 wherein said antibody-enzyme conjugates compromise enzyme-metal conjugates.

97. A method according to claim 96 wherein said enzyme-metal conjugates comprise colloidal gold and iron conjugates.

98. A method according to any of claims 3, 4, 6, or 7 wherein said detecting comprises use of antibodysensitized red blood cells.

99. A method according to any of claims 3, 4, 6 or 7 wherein said detecting comprises a cytotoxicity reaction.

100. A method according to any claims 3, 4, 6 or 7 where said detecting comprises a chemiluminescence reaction.

101. A method according to any of claims 3, 4, 6 or 7 wherein said detecting step is automated.

102. A method according to claim 100 wherein said detecting comprises mechanical pipetting of fluid samples, liquid reaction reagents, and/or secondary antibody solutions.

103. A method according to claim 101 wherein the ligand-receptor complex comprises fluorochrome dyes and said detecting comprises use of an incident light beam to excite said fluorochrome dyes.

104. A method according to claim 103 wherein said detecting comprises use of a device selected from the group consisting of an optical device, a prism device and a photomultiplier device.

105. A method according to claim 101 wherein said detecting comprises use of bound antibodies to detect cell agglutination.

106. The method according to any of claims 1, 2, 3 or 4 wherein said carbohydrate is selected from the group consisting of monosaccharides, disaccharides, trisaccharides and oliggosaccharides.

107. A diagnostic panel comprising a plurality of compartments or sectors, each containing a different lyophilized material selected from the group consisting of cell, cell membrane, lymphocytes, platelets, peripheral blood cells, stem cells, liposomes, hemosomes, cell membrane ghost, cultured mammalian cells, stroma, hybridoma cells or erythrocytes, lyophilized or dried in the presence of a cryoprotectant comprising a monosaccharide, disaccharide or trisaccharide and at least one biologically compatible amphipathic polymer, and known to have one or more antigens which are recognized and bound by a selected antibody type.

108. A panel according to claim 107 wherein each of said standard compositions is attached to said solid support through a chemical crosslinking reagent.

109. A panel according to claim 108 wherein said chemical crosslinking reagent comprises a bifunctional crosslinking reagent.

110. A panel according to claim 109 wherein said bifunctional crosslinking reagent comprises a spacer of variable length between the reactive chemical group.

111. A panel according to claim 108 wherein said chemical crosslinking reagent comprises a 20 photoactivated crosslinking reagent.

112. A panel according to claim 67 wherein said chemical crosslinking reagent is selected from the group consisting of aldehydes, maleimides, succinimides and carbodiimides.

113. A panel according to claim 112 wherein said aldehyde comprises glutaraldehyde.

114. A panel according to claim 109 wherein each of said standard compositions is attached to said solid support through an organic dye.

115. A panel according to claim 113 wherein said organic dye carries a net electric charge.

116. A panel according to claim 107 wherein each of said standard composition is attached to said support through antibodies.

117. A panel according to claim 116 wherein said antibodies comprise antibodies which recognize and bind to cell surface antigens.

118. A panel according to claim 117 wherein said antibodies comprise antibodies against mammalian cells.

119. A panel according to claim 17 wherein said antibodies are selected from the group consisting of anti-red cell antibodies, antiplatelet antibodies, antileukocyte antibodies, and antilymphocyte antibodies.

120. A panel according to claim 116 wherein said antibodies are selected from the group consisting of polyclonal antibodies and monoclonal antibodies.

121. A panel according to claim 107 wherein said standard compositions are attached to said solid support through lectins.

122. A panel according to claim 107 wherein said wherein said solid support comprises a polymer.

123. A panel according to claim 122 wherein said polymer comprises a benzene nucleus.

124. A panel according to claim 122 wherein said polymer comprises a polymer diazonium salt.

125. A panel according to claim 107 wherein said solid support comprises a plastic microplate.

126. A panel according to claim 125 wherein said microplate comprises polystyrene.

127. A panel according to claim 125 wherein said microplate comprises a diazonium salt of polystyrene.

128. A panel according to claim 108 wherein said crosslinking reagent comprises a diazoamino bond.

129. A panel according to claim 107 wherein said solid support is selected from the group consisting of glass, diazobenzylcellulose, nitrocellulose, cellulose, agar, nylon, polyvinylchloride, latex, polystyrene and polypropylene.

130. A panel according to claim 107 wherein said standard composition occupy discreet areas on a solid dipstick support.

131. A panel according to claim 107 wherein said standard composition is attached to a permeable pad.

132. A panel according to claim 107 wherein said standard composition is attached to a solid support selected from the group consisting of pellets, microspheres, and beads.

133. A panel according to claim 131 wherein said permeable pad is embedded with additional enhancing, sensitizing, or detection reagents.

134. A panel according to claim 107 wherein said material is subjected to treatments to enhance the binding of known antibody types.

135. A panel according to claim 134 wherein said material is subjected to said treatments prior to attachment to a solid support and lyophilization.

136. A panel according to claim 134 wherein said material is subjected to said treatments after attachment to a solid support, lyophilization, and rehydration.

137. A panel according to claim 134 wherein said treatments comprise exposure to an agent selected from the group consisting of proteolytic enzymes, detergents, chemical fixatives, low ionic strength saline, high ionic strength saline, and high molecular weight polymer solutions.

138. A panel according to claim 97 wherein said proteolytic enzymes are selected from the group consisting of bromelain, papain, trypsin, chymotrypsin, pronase, ficin and proteinase K.

139. A panel as in claim 107 wherein said material comprises antigens of the ABO blood antigen group.

140. A panel as in claim 107 wherein said material comprises antigens of the Rh-hr blood antigen system.

141. A panel as in claim 107 wherein said material comprises antigens of the M, N, S and PI blood antigen systems.

142. A panel as in claim 107 wherein said material antigens of the Duffy (Fy) and Kidd (Jk) blood antigen systems.

143. A panel as in claim 107 wherein said material comprises antigens of the Kell (K) and Cellano (k) blood antigen systems.

144. A panel as in claim 140 wherein said Rh-hr antigens are selected from the croup consisting of D, C, E, c, and e.

145. A panel as in claim 107 wherein said material is selected from the group consisting of HLA antigens and platelet-specific antigens.

146. A panel as in any one of claims 107, 139, 140 or 144 wherein said material comprises a control standard panel for manual or automated antibody detection assays.

147. A control panel as in claim 146 wherein said automated assay comprises use of a deceive selected from the group consisting of an automated pipetting lens or an optical lens.

148. A control panel as in claim 146 wherein said control cells are selected from the group consisting of the ABO blood groups and Rh-hr blood antigen systems.

149. A control panel as in claim 148 wherein said Rh-hr antigens are selected rom the group consisting of D, C, E, c, and e.

150. A control panel as in claim 147 wherein said control cells comprise the HLA antigen system.

151. A control panel as in claim 147 wherein said cells comprise platelet-specific antigens.

152. A diagnostic kit for detecting in vitro the presence or absence of a predetermined circulating antibody-type in a plasma or serum sample, said kit comprising a panel of a plurality of compartments, each of said compartments containing a different lyophilized material selected from the group consisting of cells lymphocytes, platelets, peripheral blood cells, stem cells, liposomes, hemosomes, cell membrane ghost, cultured mammalian cells, stroma, hybridoma cells or erythrocytes, lyophilized or dried in the presence of a cryoprotectant comprising a monosaccharide, disaccharide or trisaccharide and at least one biologically compatible amphipathic polymer and wherein each lyophilized material is characterized by one or more antigens which are recognized and bound by a predetermined antibody-type.

153. A kit according to claim 151 further comprising an enhancer for enhancing a desired antibody-antigen reaction.

154. A kit according to claim 150 wherein said enhancer comprises a polymer.

155. A kit according to claim 154 wherein said polymer comprises polyethylene glycol.

156. A kit according to claim 153 wherein said enhancer comprises a protein.

157. A kit according to claim 156 wherein said protein is bovine serum albumin.

158. A kit according to claim 153 wherein said enhancer imparts to said material, when reconstituted, a pH of about 7.2 or lower.

159. A kit according to claim 152 wherein said material is selected from the group consisting of.erythrocytes, lymphocytes, platelets, lyposomes and hemosomes.

160. A kit according to claim 151 wherein said compartments comprise microplate wells capable of being scored for agglutination.

161. A kit according to claim 151 wherein said compartments comprise chips etched with microliter or submicroliter volume wells, capable of being scored for agglutination.

162. A kit according to claim 152 wherein said lyophilized material is selected from the group consisting of beads, pellets and droplets, and said compartments comprise blister packs accommodating said material.

163. A kit according to claim 152 wherein said material comprises cell membranes.

164. A kit according to claim 163 wherein said cell membranes are mammalian cell membranes.

165. A kit according to claim 164 wherein said cell membranes are selected from the group consisting of cell membranes prepared from erythrocytes, lymphocytes, platelets, peripheral blood cells and stem cells.

* * * * *